(12) United States Patent
Van Roy et al.

(10) Patent No.: US 7,569,668 B2
(45) Date of Patent: Aug. 4, 2009

(54) METHOD TO CONTROL TUMOR PROGRESSION AND INVASIVENESS

(75) Inventors: Frans Van Roy, Destelbergen (BE); Geert Berx, Linter-Wommersom (BE); Kristin Strumane, Amsterdam (NL)

(73) Assignees: Vlaams Interuniversitair Instituut Voor Biotechnologie VZW, Zwijnaarde (BE); Universiteit Gent, Ghent (BE)

( * ) Notice: Subject to any disclaimer, the term of this patent is extended or adjusted under 35 U.S.C. 154(b) by 90 days.

(21) Appl. No.: 11/454,605

(22) Filed: Jun. 16, 2006

(65) Prior Publication Data

US 2007/0066803 A1    Mar. 22, 2007

Related U.S. Application Data

(63) Continuation of application No. 10/923,543, filed on Aug. 20, 2004, now abandoned, which is a continuation of application No. PCT/EP03/01683, filed on Feb. 18, 2003.

(30) Foreign Application Priority Data

Feb. 20, 2002    (EP)    ................... 02075657

(51) Int. Cl.
    *C07K 14/00*    (2006.01)
(52) U.S. Cl. .................................. 530/350
(58) Field of Classification Search ........................ None
    See application file for complete search history.

(56) References Cited

U.S. PATENT DOCUMENTS 6,057,101 A    5/2000    Nandabalan et al.

2003/0105000 A1 *    6/2003    Pero et al. ..................... 514/12

FOREIGN PATENT DOCUMENTS

| EP | 1 109 021 A1 | 6/2001 |
|---|---|---|
| WO | WO 94/11401 | 5/1994 |
| WO | WO 98/13502 | 4/1998 |
| WO | WO 99/20168 | 4/1999 |
| WO | WO 01/64944 A1 | 9/2001 |
| WO | WO 03/070759 A2 | 8/2003 |

OTHER PUBLICATIONS

Jaruzelska et al. (Feb. 11, 2003, Dev. Genes Evol. 213:120-126).*
Bowie et al (Science, 1990, 257:1306-1310).*
Burgess et al (J of Cell Bio. 111:2129-2138, 1990).*
Lazar et al (Molecular and Cellular Biology, 1988, 8:1247-1252).*
Scott et al. (Nature Genetics, 1999, 21:440-443).*
Bork (Genome Research, 2000, 10: 398-400).*
Strumane et al., E-Cadherin Regulates Human NanosI, which Interacts with p120ctn and Induces Tumor Cell Migration and Invasion, Cancer Res., Oct. 15, 2006, pp. 10007-100015, vol. 66, No. 20.
Jaruzelska et al., Human nanos in a gene that is upregulated in the testis and interacts with human pumilio, Abstract, XP002210395, AF275269 Dec. 2, 2001.
Comijn et al., The Two-Handed E Box Binding Zinc Finger Protein SIP1 Downregulates E-Cadherin and Induces Invasion, Molecular Cell, Jun. 2001, pp. 1267-1278, vol. 7, No. 6.
Daniel et al., The Catenin p120(ctn) Interacts with Kaiso, a Novel BTB/POZ Domain Zinc Finger Trnascription Factor, Molecular and Cellular Biology, May 1999, pp. 3614-3623, vol. 19, No. 5.
PCT International Search Report, PCT/EP03/01686, dated Sep. 2, 2003.
PCT International Preliminary Examination Report, PCT/EP03/01683, dated Jun. 8, 2004.

\* cited by examiner

*Primary Examiner*—Karen A Canella
*Assistant Examiner*—Peter J Reddig
(74) *Attorney, Agent, or Firm*—TraskBritt

(57) ABSTRACT

Described is a method of modulating E-cadherin mediated cell adhesion. More specifically, described is the use of hECRep1a and homologues thereof to modulate and/or control tumor cell invasiveness.

1 Claim, 15 Drawing Sheets

Fig. 3 (1/5)

```
  1 ggcaggccgg cgggcaggct cggcgtgtcc cttccgtccg gcccgcgccg    50

51 gcggcgggga ggcggcgcgc ggcccgcagc ccgccc atgg aggctttccc   100
                                   5'UTR ↵ ORF 101 ctgggcgccc cgctcgcccc gccgcggccg cgccccccg cccatggcgc    150

151 tcgtgcccag cgcccgctac gtgagcgccc cgggcccggc gcacccgcag   200

201 cccttcagct cctggaacga ctacctgggg ctcgccacgc tcatcaccaa   250

251 agcggtggac ggcgagccgc gcttcggctg cgcccgcggt gggaacggcg   300

301 gcggcggctc cccgccctcc tcctcctcgt cgtcctgctg ctccccccag   350

351 acggggccg ggcctggggc gctggggccg gcgctggggc cgcccgacta    400

401 cgacgaggac gacgacgacg acagcgacga gccggggtcc cggggccgct   450

451 acctggggag cgcgctggaa ttgcgcgcgc tggagctgtg cgcgggcccg   500

501 gccgaggccg ggctgctgga ggagcgcttc gccgagctga gcccgttcgc   550

551 gggtcgtgcc gccgccgtgc tgctgggctg cgcgcccgcc gccgccgccg   600

601 ccgccaccac caccagcgag gcgacgccgc gcgaggagcg ggccccggcg   650

651 tgggcggccg agccccggct gcacgcggcc tccggggcgg cggccgcccg   700

701 gctgctgaag cccgagctgc aggtgtgcgt gttctgccgg aacaacaagg   750

751 aggcgatggc gctctacacc acccatatcc tcaagggccc cgacgggcga   800

801 gtgctgtgtc ccgtgctgcg ccgctacacg tgtccctgt gcggcgccag    850
```

Fig. 3 (2/5)

```
 851 cggcgacaac gcgcacacca tcaagtactg cccgctctcc aaagtgccgc  900

901 cgccgcccgc ccgcccgccg ccccgcagcg ccagggacgg cccgcctggc  950

951 aagaagctgc gctgaaggcc cgggctcccg gccgcccagg gtcgccgccg 1000
                    ↳3'UTR 1001 cccctcgcac cgctaggtct gcgcaccatc tcgcccccgc cgtggggagg 1050

1051 cgtgcggctc agcggtcggc tcgacatggg acgtcgtcct ggtggttttt 1100

1101 gaaaagcagc cgaccgtgtg gagtacttcc gtgctgaacg attgggacta 1150
                              SSH-clone 1151 gacgctgaaa tccccatttg tcttcagttt ctagtttgca catccagaac 1200

1201 ggcgaaggct gggtgtgtat tccactaact gaaatatggc aacttagagg 1250

1251 cgctgtttat ttactgtata cgtcgaccta ttttagatgc gcatcagtat 1300

1301 gaaattgtct caatcttgga tgtttcattt tatgaatgga ggcactttac 1350

1351 taggtctaga atatttttt aaaagcctct gaactgagct taaaactggc 1400

1401 gattttatga aatgtcggca aatgactat tttattgttt gaagcgagtt 1450

1451 aatattctca gttgtctta aaaatcagtt actctaattc caggtgaagc 1500

1501 aagccgctgg tagcatcacc cttatgagaa gtgaaggttt tgtaaacttt 1550

1551 ccagtattaa tttgggcggg tattccccgc ttgtggcttg tttctgtcct 1600

1601 agctggaggt gtaaaatgca caatgtgtag caggtagaat acagctcctt 1650

1651 atcgttctat gtaccaggta ttttattact gaactagcaa ctagccttt 1700
```

Fig. 3 (3/5)

```
1701 ccacctttaa aagttgtgcc aagtcataat catattgtgt ataacttgga 1750

1751 aatggtgctg ttt aaaaaa a ttgtgtattt atacagtaac agtatgaatt 1800
              poly-A-signal 1

1801 cattaatctc|acctgtaact ttcctacttg gccttttctc tacacactca 1850
         poly-A(1)

1851 ccctcttcca gttctttaaa aacgtttatg atattaagat caaagggagg 1900

1901 aagggaagac agcagtatta attcacccta gattactcaa tttcagggtt 1950

1951 cctagtggag gaaagcccat tccagctgtt gcctgtcaaa caaatagaag 2000

2001 atggatctct agctctgagc tattcgtgta ttaactcgta ttcaagaagg 2050

2051 ttccaccgtg ggctgcgtct gactttaata caggcagtgc tcaaactaga 2100

2101 ataagcacta attaaaggaa ttgttggggg tccttcatgt gttcccactc 2150

2151 ctactggaag acccatgtcg gtttccggaa ccccaccagt ttacccataa 2200

2201 gcaagactaa acctgatcct tgggcaaaag ttcctaaccc ctactttacc 2250

2251 ctcccaccct cacttttaaa tccaccatac tgaatgccac actatggaat 2300

2301 gcagctacct gccaagcaag gcaatagaag gcaaaaaatg gaagtgaatt 2350

2351 aagatgaact catctgaaat acacaaatgc attactatct gaagatacca 2400

2401 gcaagagttt agtctacgtg tataaggctc ccagtaggat ttagctaggc 2450

2451 tactagaagt tagactgctt tcgcattaaa cagctaactt cattcacagc 2500

2501 aaattgactt aatcagaacc tttattttgn aaggtgtgtt agaaggatgg 2550
```

Fig. 3 (4/5)

```
2551 gggtccatag ctgtcttttt ggtgaaagaa aaggtgcatt tcaagaactt 2600

2601 gggggggcagg aggaaagcac aatgtttctt agccaggaaa gacaaataat 2650

2651 ccaacgctgc tagtcttaac cccagaccag agagaactgc agatctgact 2700

2701 gggcctaaat taagtagctt aatgaaacca tgtaattact tgttctcctt 2750

2751 tcttttgcta tagaaaatct accagtttaa atgagcttca ccttctgggt 2800

2801 gaagtttcta aggtcaacat gaatcctctt acctctctca ctgctcgtgt 2850

2851 tctgcctttt caaaaggacc actatgaaca gatcagcgca ttctctaggc 2900

2901 caaaagggct agccaggtgg caagatcaat ttagctactt tgtattttca 2950

2951 gagtcaaatt acagacggtt ccaaaggtc ttgagcatgg ggctttggca 3000

3001 tagcctcaat atatgggagt cactgtgatg agatgtgcct aatgttaatt 3050

3051 tgatattctg acattgctac tattttacca gaactaagaa catattgagc 3100

3101 tggagcttct tgagggcagg agagtattgg aaaaggaatc cagaagaccc 3150

3151 tctccactac tcaggcagcc actattcatc tatttttaaa gtaccccatt 3200

3201 [ALU] 3250

```
3401 aaccaggagg cggagttgc agtgagcca gatcacgcca ctgcactcca 3450
3451 gcctgggca cagagcgac ctgtctcaa aaaaaaaaa aagtacccca 3500
3501 tgttcagccc ctgtgccaaa tttgcctagg ttttccagct gacaatgaat 3550
3551 actgggagtt aaaacgcaga gtattactat agttaatttt ctagggttct 3600
3601 cttatgaaaa gtatatgtaa acacattcat ttaaaaatcc ttggaactca 3650
3651 atgtggaact ttaaacattt tgcaaaatta catttagaga aacccaattt 3700
3701 ttcaaagttt aagaaatata caaagtatga caaaattatc ttcataagaa 3750
3751 catgctgcat acttgcctag tagcaaaaca atacagggaa gagtcaaaag 3800
3801 ggcttctcca actgtagagg tacagattgt cttaacctgt tcttttctgt 3850
3851 acagacttaa aatttctagt ggcttttatt tttctttgta ttttaatttt 3900
3901 cctacaaagt ccttttgga agttgcagaa ttattagctt tgatgagaac 3950
3951 aacttttgtc atagatttga tttattaaac caaaattata cat attaaaa 4000
                                                    poly-A-signal 2
4001 ttatatcaca aatataaaaa aaaaaaaaaa aaaaa              4035
```

Fig. 4a

```
H.sapiens        1 ----------ME FPW PRSPRRGR PPPMALVPSAR VSAP PAHPQP  S  N   --
X.laevis         1 --------------- D---------- ---------------- C----   S   --
D.melanogaster   1 MFRSNLEGSGAA VG  NPPSLAQS KIFQLQDNFSA HARG NILGLQ M L TS AN H.sapiens       49 ---- AT   KAVD-------------------------------------- E
X.laevis        16 ----  S  S ------------------------------------------------
D.melanogaster  61 SSAT  PP  PVTPDPSTSAQSTHFPFLADSAATANSLLMQRQYHYHLLLQQQQQLAM Q H.sapiens       61 P  F C RG N  G  PPS SSSS-----CCSPH   P--- A GPA  G PDYDEDDD
X.laevis        22 - ---------------------------------------- -------QR
D.melanogaster 121 HQL L  AS A A SA HQQ DEIARSLKIFAQVT   ENAA S QDV  EFATNGYAS H.sapiens      113 SD--EP   GRY GSALELRALELC GPAEA ----L EE  AE  FAGRAAA -----
X.laevis        30 ------ E - ------------------------ WDV ------------
D.melanogaster 181 LGRMSY  AP Q QMPPQQQHQQQQ LHLPL RNPAQ QTNG N M IPLATHW NNYRE H.sapiens      162 ----------L GC ------ A  AT  S ATPREERA AW AEP LHAA  AAAAR
X.laevis        41 ---------------------- S EP PS  S ----------------HK -----
D.melanogaster 241 HLNNVWRNMSY PA  NTMGLQ  QT  TVS  LG  MGLGL VQ EQL GASN SNNNNN H.sapiens      206 ----------LL PELQV                                         
X.laevis        57 ----------------                                         N
D.melanogaster 301 NNKVYKRYNSKA EISRH    E  N PE IN SV DNFN    K  T V   I H.sapiens      256     I   C   SKVPPPPARPP R A D  P---G K  -
X.laevis        99  W  TMR    RRL RD----- Q NSNN -----  H
D.melanogaster 361 S         K P  TMEDAIKAE F L KSSYYKQQ   V
```

Fig. 4b

```
hECRep1a   1 MEAFPWAPRSPRRGRAPPPMALVPSARYVSAPGPAHPQ  SS N    T TKA DG
hECRep1b   1 ------------------------------MQ P  M K  FN  Q  W  SR
hECRep1c   1 ------------------------------ GT  L  T     H  R  S K hECRep1a  61 PRFGCARGGNGGGGSPPSSSSSSSCCSPHTGA  GALGPA G PDYDEDDD SD  GSRG
hECRep1b  27 --------------------------------- Q  ET-------- EI  ----
hECRep1c  25 ---------------------------------ET S--------  PEP  ---- hECRep1a 121 RYLGSALELRALELCA  AE GLLEERFAE S  E GRAAAVLLGC  A A  ATTTSEAT
hECRep1b  39 ---------------SP----------- LG---------QDQ LG  ANG---
hECRep1c  39 ---------------MLE VS--------  E  P-------- ES PV  PKDQKR hECRep1a 181 PREERAPAWAAEPR HAASGAAAARLLKPELQ V  RN K AM L TT I  G
hECRep1b  58 ------------G G----------------- N       HV S  Q  T   V
hECRep1c  66 -------------S E SP---------APER  S           I Q  V  DEA hECRep1a 241  V R T L  S  N   I   SKVPPPPARPP   A  GPP     R--------
hECRep1b  90      H   V  S  Q  TL   N - QQ  L R--  G -   RRVK------
hECRep1c 104    D   Q   RER  RRF  T Q YT V S--HTT  -   V PDKAKTQ hECRep1a     ------------------------
hECRep1b     ------------------------
hECRep1c 161 DTGHRRGGGGGAGACTGGWGGPVRG
```

Fig. 4c h/m/rECRep1a

```
H.sapiens      1   EAFIWAPRSFPPGRALPIKALPGAFTCCPPPAIQTTHTTCLAFITKVGE
M.musculus     1   EAFIWAPRSFPRAFAFAPIIALVISAFTISASGFTHEQIFLWNTLJLAFIT----
R.norvegicus   1   EAFIWAPRSFPRAFAFAPIIALVFSAFYVSASGFVHICEFYITLATILG----

H.sapiens     61   PRFGCA GNGGGGSPPSSSSSSCC  T A G L A   DYDE D   S   GSR
M.musculus    59   ------ ------------------HESIGETFAGSFTM--     E      
R.norvegicus  59   ------ ------------------IHFGESE P  ETIGI H.sapiens    121       S LELRALELCAGIAES LLEERFAEL S  A P ERATLL   A A--   TT S
M.musculus    94       LRALELRALELCAGIAE P LLEERFAELNN FASPAAATLL  T TT     
R.norvegicus  94       I FLRALELCAGIAE P LLEERFAEL   F  AAAV    S   ----

H.sapiens    179   A  I  RA AWAAEI RLHAA  A AR LLKEEL  TF RHHAEAMAT I HLP H
M.musculus   154       TFREEL PAWAAKFFLSAASOATAARLLKEELN  VFOHHFEATAI TTHI LF
R.norvegicus 150       TFRREEINPAWAAEPF  HA T    TARLKEELO TFPHUNEA AL TTHI P H H.sapiens    239   LTEVLKF YTCELV GA VHLHAHTIKV ILSKVFH  PA I PA GP G
M.musculus   214   I TF LRF YTCELV GASGDHAHTIKV ELSKV IL H      N   S
R.norvegicus 210   L PE LRFYTCELV GASGDHAHTIKV ELSKV H ETVF L    T  N
``` h/m/rECRep1b

```
H.sapiens      1   Q  F  K  T H       WAL A G    T EI   SPG PLGQD   GAPGAN G G
M.musculus     1         FI  LTF         MD I  ER  Q G  A   N  I EK     D  Y-- C
R.norvegicus   1        R   T           LG        D  S  LA   GM  R   VS-- S H.sapiens     61   L   F  H P GP H  S     PT D    GEILF T  TV           GG
M.musculus    59   I    F  H   RSRH TT  LFTI L    G  ILF         GAI  I
R.norvegicus  59   A                     NKTI P    EILF H    G  I H.sapiens    121   
M.musculus   119   
R.norvegicus 119   
``` h/m/rECRep1c

```
H.sapiens      1      D       L H  R  SGK G ET   S Q   EPMLEPVSALEPMPAPESVPV GP
M.musculus     1                      K   L                  -------------------
R.norvegicus   1                      E                      -------------------

H.sapiens     61   KD KR L    P       SF RHH LCRA     LR EAGF L T I             R
M.musculus    41   E   A KF  A  F  C  H I  TECFAI   H ESHEA PF L               W
R.norvegicus  41   A   A PF  A F       C                 IN F                   W H.sapiens    121   R        FL T       SH  F L A    V        T  R  G G   ACT W
M.musculus   101            F   S       I                                      L
R.norvegicus 101         F  FL T              F  PLTF  AFT N                --

H.sapiens    181   GPV G-------
M.musculus   161   VGW RLSVFWGV
R.norvegicus       ------------
```

Fig. 6
a
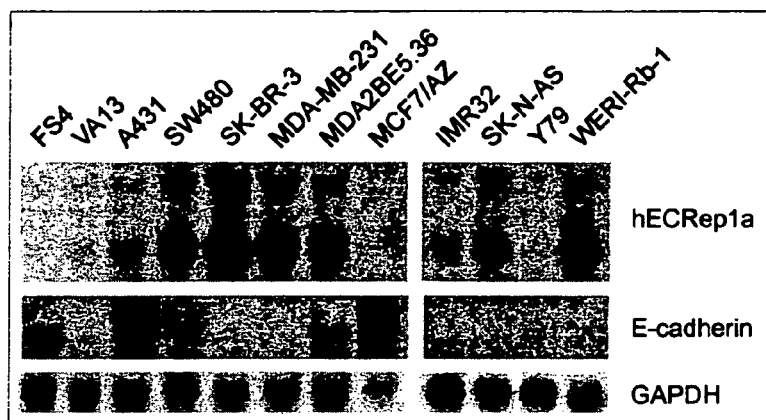
b
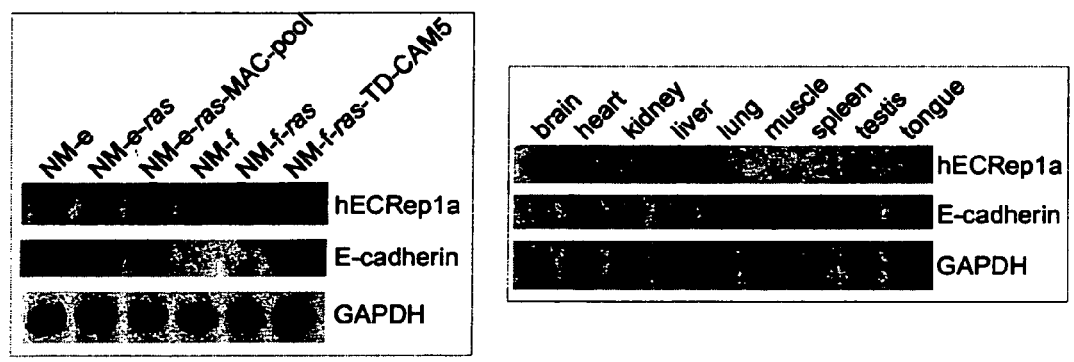
Fig. 7
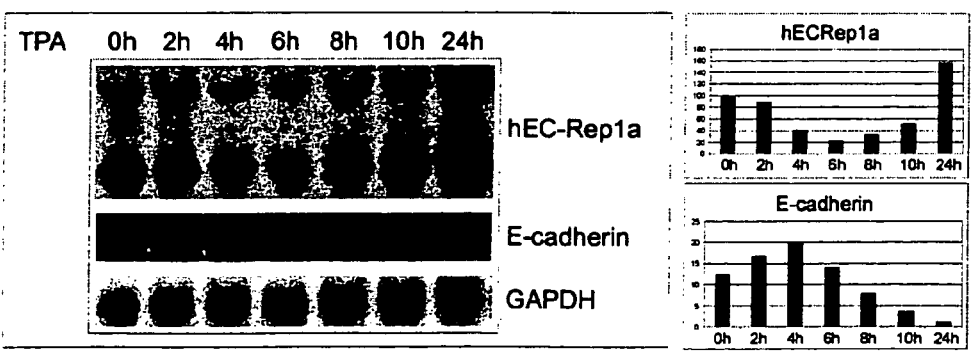

Fig. 10
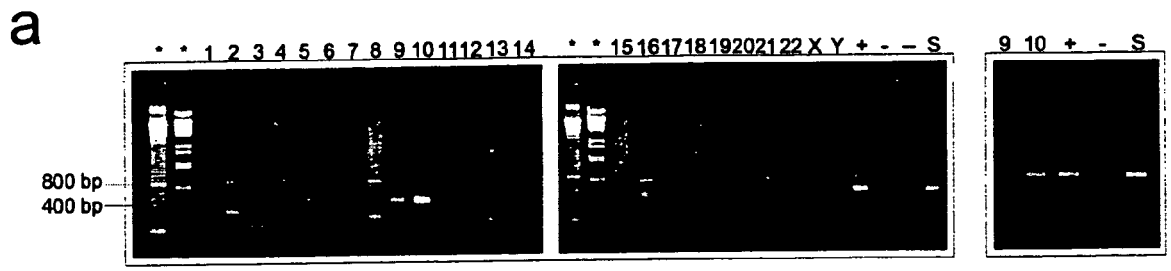
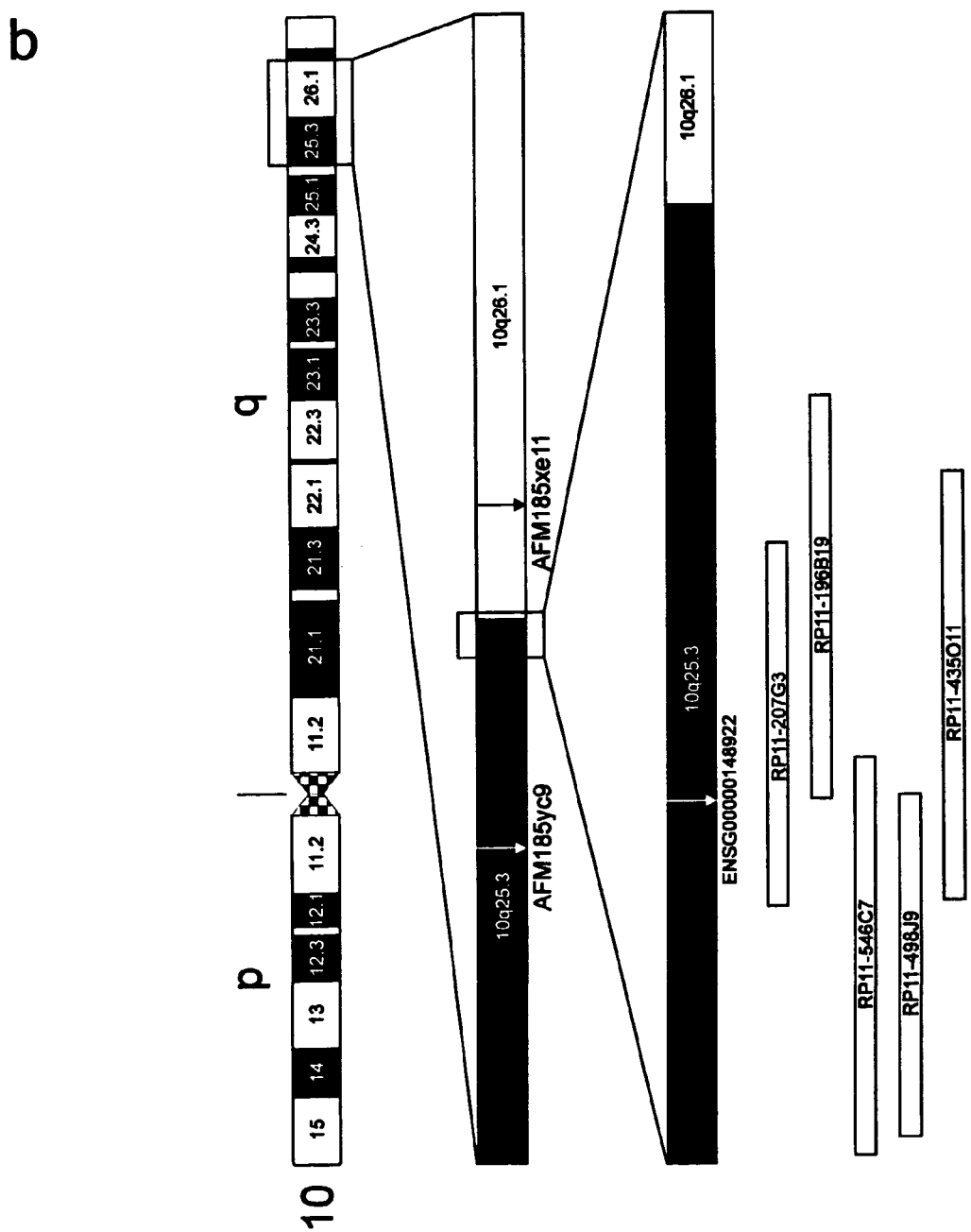

Fig. 12
a
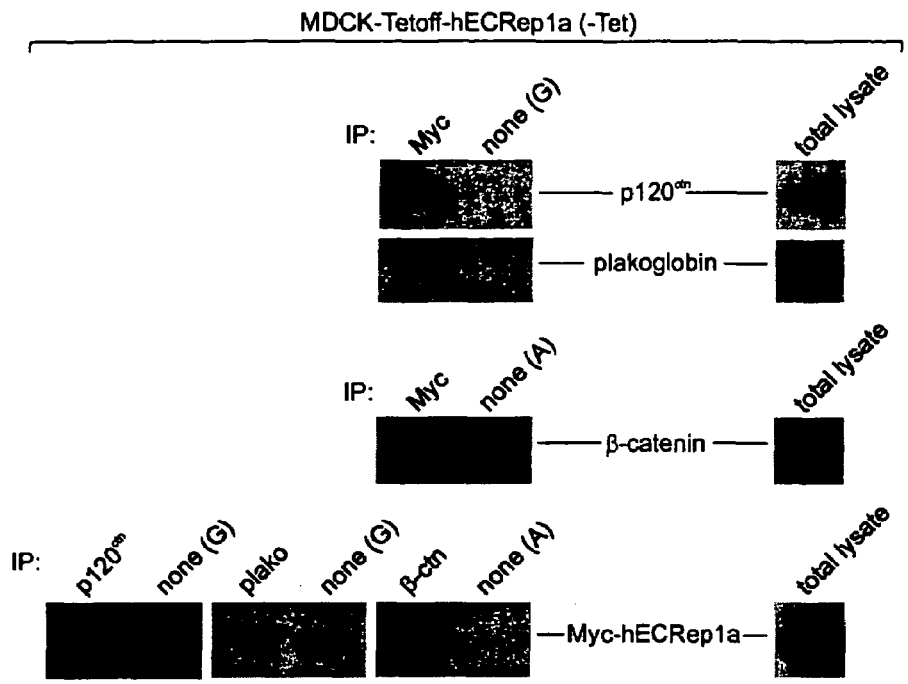
b
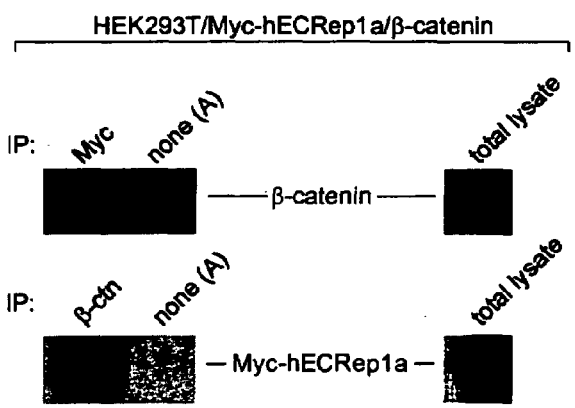
c
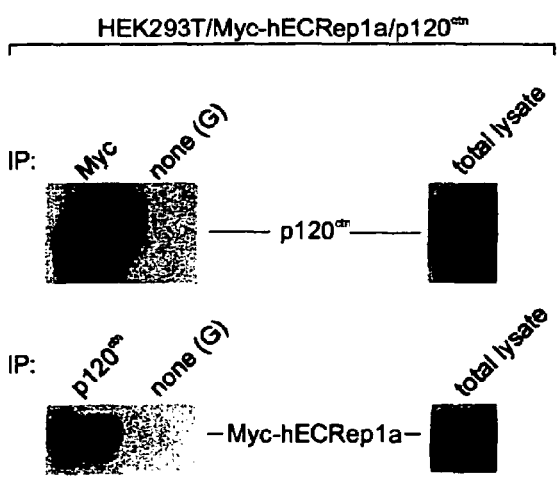

Fig. 13
a
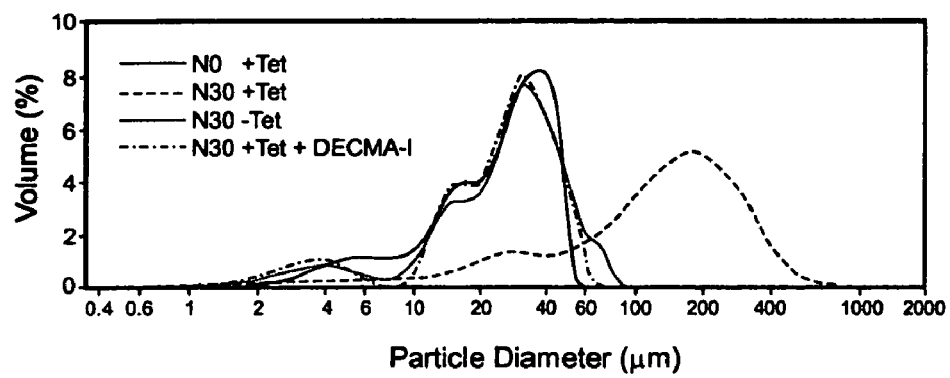
b
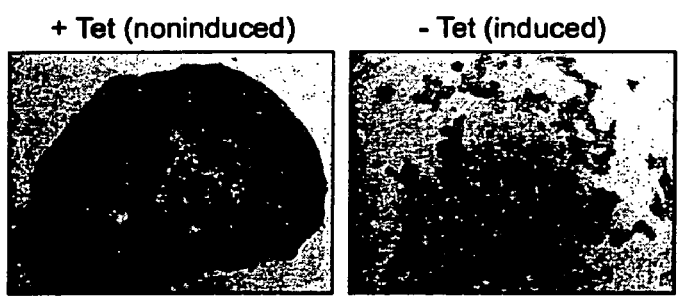
c
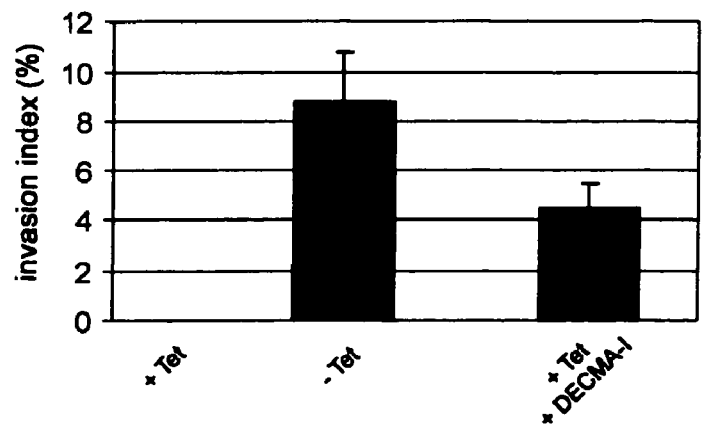

METHOD TO CONTROL TUMOR PROGRESSION AND INVASIVENESS

CROSS-REFERENCE TO RELATED APPLICATION

This application is a continuation of U.S. patent application Ser. No. 10/923,543, filed Aug. 20, 2004, and published on Apr. 28, 2005 as US20050089896A1, now abandoned, which is a continuation of PCT International Patent Application No. PCT/EP03/01683, filed on Feb. 18, 2003, designating the United States of America, and published, in English, as PCT International Publication No. WO 03/070759 on Aug. 28, 2003, which claims the benefit of, the filing date of EP02075657, filed Feb. 20, 2002, the contents of the entirety of each of which are incorporated by this reference.

TECHNICAL FIELD

The present invention relates generally to biotechnology, and more particularly to methods modulating the E-cadherin mediated cell adhesion. More specifically, the invention relates to the use of hECRep1a and homologues thereof to modulate and/or control tumor progression and tumor cell invasiveness. Moreover, the present invention identifies hECRep1a and homologues as targets for therapy directed against human tumors, more particularly malignant tumors.

BACKGROUND

E-cadherin is a transmembrane molecule that forms a protein complex with cytoplasmic catenins in the zonula adherens of epithelial cells, where it has an established function in cell-cell adhesion. β-catenin binds via its armadillo-repeats directly to the C-terminal tail of E-cadherin (Stappert and Kemler, 1994). The vinculin homolog α-catenin establishes a link to the actin cytoskeleton by binding to the N-terminal part of the E-cadherin-bound β-catenin on the one hand (Jou et al., 1995), and to F-actin or an actin-bound α-actinin dimer on the other hand (Knudsen et al., 1995; Rimm et al., 1995). Proper formation of this E-cadherin/catenin-complex has been shown to be crucial for normal early embryonic development as well as for the maintenance of differentiation, polarization and integrity of adult epithelial tissue structures (Behrens et al., 1989; McNeill et al., 1990). p120ctn is another Armadillo catenin that binds to the membrane-proximal cytoplasmic part of E-cadherin (Daniel and Reynolds, 1995), which is involved in the establishment of strong E-cadherin-mediated cell-cell adhesion (Thoreson et al., 2000). As the presence of a functional E-cadherin/catenin-complex is a prerequisite for normal development and maintenance of epithelial structures in the mammalian body, acquisition of molecular abnormalities in one of the elements of this complex are related to the development and progression of epithelial cell-derived tumors, i.e., carcinomas.

Suppression of the E-cadherin/catenin-complex leads to invasion and metastasis. E-cadherin has been shown to be a potent invasion suppressor (Frixen et al., 1991; Vleminckx et al., 1991) as well as a genuine tumor suppressor (Berx et al., 1995; Berx et al., 1996). Loss of E-cadherin expression is reported for at least fifteen types of carcinomas (Potter et al., 1999) and is correlated with the loss of intercellular adhesion, increased cellular motility, changes in the organization of the actin filaments and a scattered growth pattern of the carcinoma cells (Handschuh et al., 1999). PCT International Patent Publication No. WO9411401 claims, amongst others, the use of E-cadherin to treat malignancies and to detect metastatic potential. PCT International Patent Publication No. WO9920168 describes the analysis of germline mutations for detecting predisposition to cancer. Besides mutational inactivation of the E-cadherin gene, which is so far restricted to infiltrative lobular breast and diffuse gastric carcinomas (Becker et al., 1994; Berx et al., 1996; Berx et al., 1998), transcriptional downregulation is the major cause of loss of E-cadherin expression in human carcinomas. PCT International Patent Publication No. WO0102860 describes the use of Snail, a transcription factor that acts as a repressor of the expression of E-cadherin, in tumor control and as diagnostic marker. As catenins are indispensable for E-cadherin functionality, loss of α-catenin or β-catenin also induces invasion of carcinoma cells (Vermeulen et al., 1999).

The key question is whether the observed role of the E-cadherin/catenin-complex in tumor growth and invasion is the direct result of its function in cell-cell adhesion or whether a more complex signaling pathway may be involved. Indeed, β-catenin and p120ctn can, when they are not bound to E-cadherin, translocate to the nucleus where they bind via their armadillo-repeats to the transcription factors LEF-1 and Kaiso, respectively (Behrens et al., 1996; Daniel and Reynolds, 1999; Huber et al., 1996). In particular, the formation of the β-catenin/LEF-1 heterodimer and the subsequent effect on transcriptional regulation are the main events of the transmission of the canonical Wnt signaling cascade to the nucleus (Miller et al., 1999). In this facet of β-catenin function, β-catenin is part of another cytoplasmic multiprotein complex, consisting of APC (Adenomatous Polyposis Coli protein), axin or conductin, and GSK3β. Without Wnt signal, β-catenin in this complex is phosphorylated by GSK3β on specific Ser-residues and in this way targeted for ubiquitin-triggered degradation. Upon binding of secreted Wnt molecules to their transmembrane Frizzled receptors, Disheveled protein will inhibit the kinase GSK3β. This results in the stabilization of cytoplasmic β-catenin that now can translocate to the nucleus and bind LEF-1. E-cadherin and LEF-1 form mutually exclusive complexes with β-catenin. E-cadherin has the potent ability to recruit β-catenin to the cell membrane and to prevent in this way its nuclear localization and transactivation activity (Orsulic et al., 1999; Sadot et al., 1998). On the contrary, E-cadherin may regulate the activity of β-catenin through mechanisms other than this canonical membrane sequestration/nuclear localization (Gottardi et al., 2001).

Recently, a novel phosphorylation-independent pathway for β-catenin degradation was described, affecting the activity of β-catenin-dependent transcription (Liu et al., 2001; Matsuzawa and Reed, 2001). In the latter pathway, β-catenin is part of yet another multiprotein complex involving Siah-1 binding to APC. Siah-1, the mammalian product of a p53 inducible growth arrest gene, is the homolog of the *Drosophila sina* (seven in absentia) gene (Hu et al., 1997). In order to target other proteins for ubiquitin-proteasome-mediated degradation, Siah-1 binds target proteins via its carboxy-terminal domain while association with ubiquitin-conjugating enzymes occurs via an amino-terminal RING domain (Hu and Fearon, 1999). Abnormal stabilization of β-catenin was shown to be involved in tumorigenesis (Gumbiner, 1997; Morin et al., 1997; Peifer, 1997; Rubinfeld et al., 1997). For colon cancer in particular, oncogenic forms of β-catenin were found in which GSK3β-targeted Ser residues are lost by mutation, thus preventing degradation of cytoplasmic and nuclear β-catenin and leading to activated Tcf/LEF target genes. Also truncation mutations of the APC gene were reported to yield the same stabilizing effect on β-catenin as these truncated APC molecules lost their β-catenin binding sites.

Also the binding of E-cadherin to p120ctn has been shown to be mutually exclusive with the interaction of p120ctn with Kaiso (Daniel and Reynolds, 1999). Like for β-catenin, E-cadherin has the potent ability to recruit p120ctn to the cell membrane and to prevent in this way its nuclear localization and potential transactivation activity (van Hengel et al., 1999). Moreover, p120ctn overexpression disrupts actin stress fibers, which correlates with reduced Rho activity (Anastasiadis et al., 2000; Noren et al., 2000). Also E-cadherin binding and the ability of p120ctn to affect Rho are mutually exclusive events (Anastasiadis and Reynolds, 2001). Assuming that an equilibrium exists between the cadherin-bound pool and the cytosolic pool of p120ctn, E-cadherin expression could regulate Rho-activity and hence actin reorganization and cell motility via p120ctn.

DISCLOSURE OF THE INVENTION

A possible crosstalk between the different multiprotein complexes involving E-cadherin and catenins can form the link between cell adhesion and signaling pathways that are involved in developmental and tumorigenic processes. Here we report the cloning of hECRep1a or hNanos1, as it is a human homolog of the *Drosophila* gene nanos. Expression of hECRep1a is down regulated by E-cadherin expression. Surprisingly, we found that the hECRep1a protein interacts with β-catenin, plakoglobin and p120ctn and that ectopic hECRep1a expression inactivates E-cadherin functionality and induces invasion in vitro. hECRep1a acts as a link between the E-cadherin cell adhesion complex and protein complexes involved in cancer development and progression. hECRep1a has two more homologues in man, designated hECRep1b (or hNanos2) and hECRep1c (or hNanos3), and also in mouse three nanos-related genes exist. The three human genes and encoded proteins are collectively called hECRep1.

A first aspect of the invention is the use of an hECRep1 protein, and/or the gene encoding this protein, and/or a functional fragment of this gene or this protein to modulate E-cadherin mediated processes. Preferably, the hECRep1 protein comprises a sequence selected from the group consisting of SEQ ID NO: 2 (of the specifically incorporated by this reference Sequence Listing), SEQ ID NO:4 and SEQ ID NO:6. More preferably, the hECRep1 protein is essentially consisting of a sequence selected from the group consisting of SEQ ID NO: 2, SEQ ID NO:4 and SEQ ID NO:6. Most preferably, the hECRep1 protein consists of a sequence selected from the group consisting of SEQ ID NO: 2, SEQ ID NO:4 and SEQ ID NO:6.

Another aspect of the invention is the use of a gene, encoding an hECRep1, or a functional fragment of the gene as a tumor marker. More specifically, hECRep1 can be used to determine the invasive and/or metastatic capacity of a tumor. Indeed, it is shown in this invention that overexpression of hECRep1 is disturbing E-cadherin mediated cell adhesion and promotes invasion. The level of hECRep1 expression in tissue can be determined and compared with the level in healthy tissue. In case of a tumor, the expression level in the tumor can be compared with the expression level in the non-affected tissue. Comparison of the expression levels can be done with the methods known to the person skilled in the art. As a non-limiting example, Northern hybridization or quantitative PCR can be used.

Alternatively, the level of hECRep1 protein production may be used to determine hECRep1 expression. Protein production can be measured with all methods known to the person skilled in the art. As a non-limiting example, antibodies, preferably monoclonal antibodies may be used to set up an ELISA test. Therefore, another aspect of the invention is the use of an hECRep1 protein, or a functional fragment thereof, as a tumor marker. More specifically, hECRep1 protein, or a functional fragment thereof can be used to determine the invasive and/or metastatic capacity of a tumor.

Another aspect of the invention is the use of hECRep1protein and/or an hECRep1 gene, or functional fragments thereof, to screen compounds limiting tumor progression and/or metastasis. Indeed, it is known that hECRep1 interacts with β-catenin, plakoglobin and p120ctn. Any compound disturbing this interaction may affect the biological function of hECRep1. As a non-limiting example of such compound, a peptide comprising one or more ARM repeats of β-catenin may be used, as it might act as a competitive inhibitor of the hECRep1-β-catenin interaction. Alternatively, a peptide that reacts with the conserved zinc finger domain of the hECRep1 proteins may affect their biological function.

Screening of compounds that inhibit protein-protein interaction is known to the person skilled in the art. As a non-limiting example, this screening may be carried out by coimmunoprecipitation, by adding the compound either to cell lysates of MDCK-Tetoff-hECRep1a cells with induced hECRep1a expression (−Tet), or from cell lysates of HEK-293T cells transiently cotransfected with pCS3hECRep1a and an expression vector for an armadillo protein (β-catenin or p120ctn). Alternatively, other screening systems for screening compounds interrupting protein-protein interaction may be used, such as, as a non-limiting example, the methods described in PCT International Patent Publication No. WO9813502 and in U.S. Pat. No. 6,057,101.

A preferred embodiment is a method for identifying a compound that limits tumor progression and/or metastasis, comprising a) setting up a protein-protein interaction screen, using an hecRep1 protein or a functional part thereof as a bait, b) adding one or more compounds to be tested to the screen, and c) scoring those compounds that interrupt the protein-protein interaction. As mentioned above, methods to screen protein-protein interactions, and compounds that interrupt these interactions are known to the person skilled in the art and have been described, as a non-limiting example, in PCT International Patent Publication No. WO9813502 and in U.S. Pat. No. 6,057,101.

Still another aspect of the invention is the use of hECRep1 expressing cells to screen compounds restoring cell adhesion and/or inhibiting invasiveness. Preferably, the cells are mammalian cells. A preferred embodiment is the use of MDCK-Tetoff-hECRep1a cells with induced hECRep1a (−Tet), that have lost their normal cell-cell aggregation, as can be measured in a fast aggregation assay in suspension (Bracke et al., 1993). Addition of the compounds to be screened before or during the assay will result in a restoration of the cell adhesion in case of a positive read out. Preferably, the compound to be screened is added 30 minutes before aggregation. Alternatively, other aggregation assays may be used, such as the slow aggregation assay described by Boterberg et al. (2001).

Another aspect of the invention is a method for identifying a compound that limits tumor progression and/or metastasis, comprising a) treating hECRep1 expressing cells with the compound to be screened, and b) scoring differences in cell adhesion and/or cell invasiveness between treated and non-treated cells. Treating of the hECRep1 expressing cells is by adding the compound as described above. In a preferred embodiment, MDCK-Tetoff-hECRep1a cells are used.

Still another aspect of the invention is a method for the production of a pharmaceutical composition comprising a method for identifying a compound according to the invention and furthermore mixing the compound identified with a pharmaceutical acceptable carrier.

BRIEF DESCRIPTION OF THE FIGURES

FIG. 3 Sequence of the human hECRep1a cDNA (SEQ ID NO:1). Boxed sequences correspond with the predicted open reading frame (ORF), the Alu-repeat sequence (ALU) in the 3' UTR and the two poly-adenylation signals poly-A-signal 1 and poly-A-signal 2,respectively. Poly-A(1) indicates the position of the start of the poly-A tail corresponding with the poly-A-signal 1. The sequence of the cDNA clone that was isolated in the initial SSH-analysis is underlined.

FIG. 4 Clustal W alignments of Nanos-related proteins in various species. (a) Alignment of the complete hECRep1a protein (*Homo sapiens*) (SEQ ID NO:2) with Xcat-2 (*Xenopus laevis*) (SEQ ID NO:15) and Nanos (*Drosophila melanogaster*) (SEQ ID NO:26). (b) Alignment of human hECRep1a (SEQ ID NO:2) with the predicted amino acid sequences of human hECRep1b (SEQ ID NO:4) and -c.SEQ ID NO:6) (c) Alignments of human hECRep1a (SEQ ID NO:2), -b (SEQ ID NO:4) and -c (SEQ ID NO:6) with their corresponding predicted mouse (mECRep1a (sEQ ID NO:17), -b (SEQ ID NO:19) and -c) (SEQ ID NO:21) and rat (rECRep1a (SEQ ID NO:18), -b (SEQ ID NO:20) and -c) (SEQ ID NO:22) orthologs. Identical and similar amino acids are labeled in black and grey, respectively. Dashes indicate gaps introduced to maximize the alignment.

FIG. 6 hECRep1a mRNA expression profiles. (a) Endogenous human hECRep1a mRNA levels were measured by Northern blotting. Strong hECRep1a expression was detected in E-cadherin-deficient cell lines only. FS4 and VA13 are fibroblast cell lines; A431 is an epidermoid cancer cell line; SW480 is a colon carcinoma cell line; MDA-MB-231, MDA2BE5.36 and MCF7/AZ are breast carcinoma cell lines; IMR32 and SK-N-AS are neuroblastoma cell lines; Y79 and WER1-Rb-1 are retinoblastoma cell lines. (b) Expression of endogenous mECRep1a mRNA in mouse cell lines and tissues was analyzed by Northern blotting. mECRep1a mRNA was detected in various mouse cell lines derived from normal mammary gland cells NMuMG (left panel) and in brain tissue (most right panel). In both (a) and (b) thirty micrograms of total RNA were loaded per lane. GAPDH, RNA-loading control.

FIG. 7 TPA treatment alters endogenous hECRep1a mRNA expression levels in SW480 cells. hECRep1a and E-cadherin mRNA expression levels were measured by Northern blot analysis. Subconfluent SW480 cells were treated with TPA and cells were lysed at different time points as indicated. Thirty micrograms of total RNA was loaded per lane. Graphic bars represent mRNA expression levels, obtained from quantification of signals on Northern blot and normalized for RNA loading based on GAPDH mRNA expression levels.

FIG. 10 Mapping of the human hECRep1a gene to chromosomal region 10q25.3. (a) PCR amplification of a hECRep1a-specific fragment of 464 bp using genomic DNA from a human monochromosomal cell-hybrid mapping panel as template. PCR was performed on cell hybrids containing each time the human chromosome indicated on top of the lanes; +, total human genomic DNA; S, total SK-BR-3 genomic DNA; –, total hamster genomic DNA; --, total mouse genomic DNA; *, size marker lanes. Amplification on human chromosome 9 (left panel) was not reproduced in a second experiment (most right panel). (b) PCR analysis of the Whole-genome Genebridge 4 Radiation Hybrid DNA panel for a hECRep1a-specific fragment revealed that the hECRep1a gene is most likely mapped between the two microsatellite anchor markers AFM185yc9 on 10q25.3 (white arrow) and AFM285xe11 on 10q26.1 (black arrow). Mapping of genomic clones that comprise hECRep1a sequences (RP11-*) fixes the chromosomal localization of the human hECRep1a gene to 10q25.3. The white arrow ENSG00000148922 indicates the position of the gene annotated as XCAT2 by the Ensemble analysis pipeline.

FIG. 12 Coimmunoprecipitation (IP) experiments showing interaction between hECRep1a on the one hand, and β-catenin, plakoglobin or p120ctn on the other hand. (a) Lysates from MDCK-Tetoff-hECRep1a cells with induced expression (−Tet) of Myc-tagged hECRep1a. (b) Lysates from HEK293T cells cotransfected with plasmids encoding either Myc-tagged hECRep1a (pCS3hECRep1a) or β-catenin (pCS2βctn). (c) Lysates from HEK293T cells cotransfected with plasmids encoding either Myc-tagged hECRep1a or p120ctn isoform 3A (pEFBOSp120-3A; van Hengel et al., 1999). The Western blots (most right lanes) serve as controls for efficient expression. IP results (left lanes) were obtained by use of monoclonal anti-Myc antibody 9E10 (Evan et al., 1985), polyclonal anti-β-catenin antibody (Sigma), monoclonal anti-p120ctn antibody pp120 (Transduction) or monoclonal anti-plakoglobin antibody PG5.1 (Cymbus). As a negative control, lysates were incubated without antibody (lanes labeled none). The A or G between brackets indicates the use of protein-A or -G Sepharose beads in that particular immunoprecipitation. SDS-PAGE was followed by Western blotting. For β-catenin, plakoglobin and p120ctn detection, blots were probed with the same antibodies as used for IP. For detection of Myc-hECRep1a on blot, an HRP-coupled monoclonal anti-Myc antibody (Invitrogen) was used.

FIG. 13 hECRep1a induction in canine MDCK-Tetoff-hECRep1a cells leads to loss of cell-cell aggregation and induction of invasion. Non-induced (+Tet) cultures were compared with induced (−Tet) hECRep1a-expressing cultures of MDCK-Tetoff-hECRep1a cells. (a) Fast aggregation assay. No cell aggregates were detected in liquid cell suspensions at time 0 (N0). After 30 min, cell-cell aggregation was readily detected for non-induced cells (N30+Tet). In contrast, hECRep1a induction abrogated such cell-cell aggregation (N30−Tet). The E-cadherin blocking antibody DECMA-I was used as a control for inhibition of aggregation. (b) Slow aggregation assay on top of an agar gel. hECRep1a induction results in loss of cell-cell contacts at 48 h. (c) Invasion into type-I collagen is induced by hECRep1a expression (−Tet). Induction of invasion by E-cadherin blocking antibody DECMA-I acts as positive control.

DETAILED DESCRIPTION OF THE INVENTION

Definitions

Figure 1:
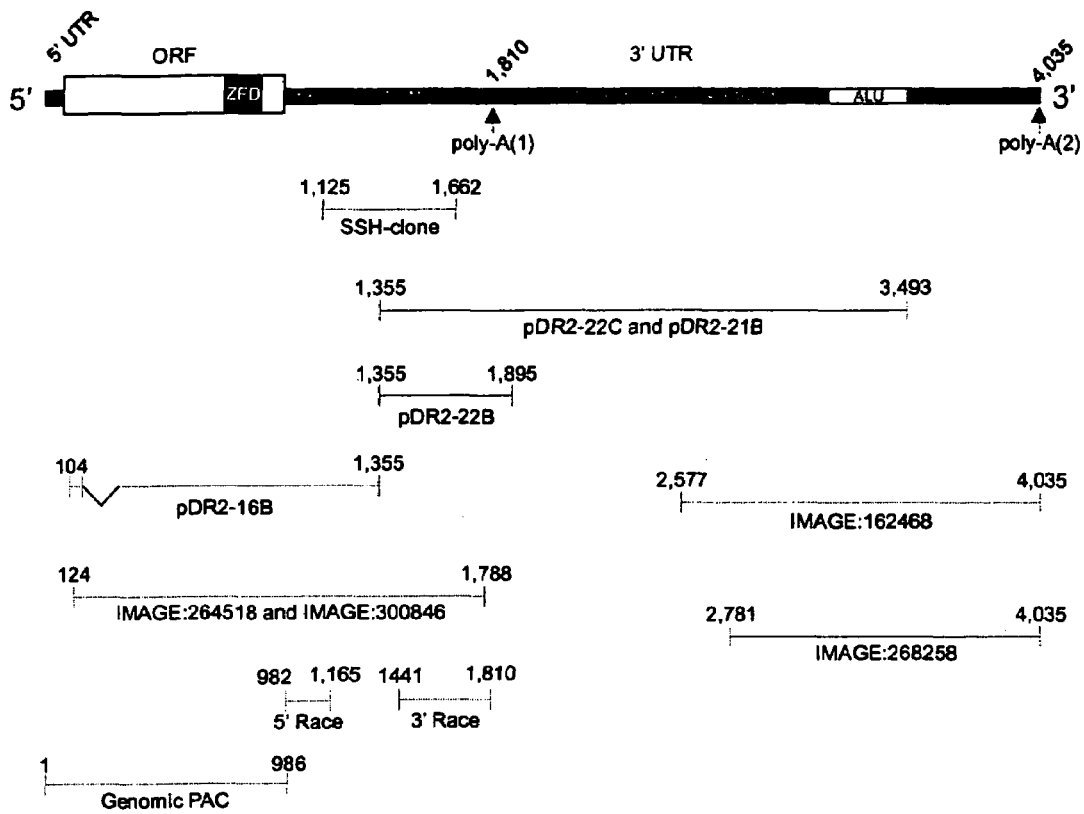
FIG. 1 Schematic representation of the human hECRep1a cDNA. The cDNA contains 86 base pairs (bp) of 5' UTR (grey box). The 876-bp long open reading frame (white box) is followed by 3,073 bp of 3' UTR (grey box). The black box within the coding region depicts the position of the (CCHC)$_2$ zinc finger domain (ZFD). The white box within the 3' UTR depicts the position of Alu-repeat sequences. The arrows poly-A(1) and poly-A(2) point at the end of the shorter transcript of 1,810 bp and of the longer transcript of 4,035 bp, respectively. The location of the sequences of the original Suppression Substractive Hybridization (SSH)-clone, of phage library clones (pDR2-16B, -21B, -22B and -22C), of EST-clones (IMAGE:264518, IMAGE:300846, IMAGE:162468 and IMAGE:268258) and of 5' and 3' Race clones are as indicated. The cDNA-sequence at the 5' end was deduced from genomic sequence data from a PAC-clone.

An "hECRep1" protein as used here indicates the hECRep1-a, -b, and -c proteins as shown in SEQ ID NOS:2, 4, and 6 of the Sequence Listing incorporated herein, and any other functional homologue thereof. A functional homologue is a protein that can complement a knock-out mutation of any of the mentioned hECRep1 encoding genes. Preferably, the functional homologue is a protein comprising the sequence CPXLRXYXCPXCGAXXXXAHTXXXCP (SEQ ID NO:7), wherein amino acid residues are indicated by universal single-letter codes and X can be any amino acid residue.

Gene as used here includes both the promoter region of the gene as well as the coding sequence and the flanking 5' and 3' untranslated regions (UTRs). It refers both to the genomic sequence (including possible introns) as well as to the cDNA derived from the spliced messenger, operably linked to a promoter sequence.

Coding sequence is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

Promoter region of a gene as used here refers to a functional DNA sequence unit that, when operably linked to a coding sequence and possibly placed in the appropriate inducing conditions, is sufficient to promote transcription of the coding sequence.

Operably linked refers to a juxtaposition wherein the components so described are in a relationship permitting them to function in their intended manner. A promoter sequence "operably linked" to a coding sequence is ligated in such a way that expression of the coding sequence is achieved under conditions compatible with the promoter sequence.

A functional fragment of a gene refers to a fragment that can be used in a functional way. Typical functional fragments are the promoter region and the coding sequence. However, functional fragment as used here means also a fragment that allows specific detection of the gene or of its messenger RNA, for example, as a probe in a hybridization experiment or as primer in a PCR reaction.

A functional fragment of the hECRep1 protein as used here refers to those domains of hECRep1 that are essential for its functionality; it does not mean that the functional fragment on its own will perform the function of the full-size hECRep1 protein. However, deletion of the domain results in one or more defects of the functionality of hECRep1. Typical functional fragments are the domains that are interacting with β-catenin, plakoglobin or p120ctn.

The invention is further described by the use of the following illustrative examples.

EXAMPLES

Material and Methods to the Examples

SSH Analysis

Polyadenylated mRNA obtained from subconfluent cells was isolated using the Fast Track® 2.0 Kit (Invitrogen) in accordance with the recommendations of the manufacturer. SSH was performed with the PCR-Select™ cDNA Subtraction Kit (Clontech) as described by the manufacturer's protocol with the following modifications: starting material consisted of 2 μg tester and 2 μg driver mRNA. Twenty units RNase block (Stratagene) were added to the first strand cDNA synthesis reaction. By adding 5 μCi [α-$^{32}$P]-dCTP (Amersham Pharmacia Biotech), the radioactively labeled cDNA could be measured in the next steps of the procedure. All PCR reactions were performed on a Perkin Elmer DNA GeneAmp 2400 PCR System using Advantage™ KlenTaq polymerase Mix (Clontech). The primary PCR was performed using 27 cycles with annealing and extension times of 30 s and 1.5 min, respectively. Four individual primary PCR reaction mixtures were pooled and diluted to a final dilution of 1/250 followed by 15 cycles of nested PCR amplification. The PCR products were size-fractionated after electrophoresis on 2% agarose gels (Sephaglas™ BandPrep Kit, Amersham Pharmacia Biotech). The obtained smear of nested PCR-products was divided into 14 fractions. Each fraction was reamplified in 10 to 15 PCR cycles using nested PCR primers. After purification (Qiaquick PCR-purification Kit, Qiagen) these PCR products were subcloned into the pGEM®-T vector (Promega). Per fraction, 192 individual clones were isolated for both the E-cadherin-induced and the E-cadherin-repressed subtracted libraries and subjected to a further differential screening using plus/minus colony hybridization. To this end, individual transformants were isolated from white colonies on X-Gal/IPTG agar plates and spotted in duplicate on Hybond N+ nylon filters (Amersham Pharmacia Biotech) using an automatic colony picker & gridder robot (PBA Flexys™). Duplicate colony filters were hybridized with either E-cadherin-repressed or E-cadherin-induced subtracted cDNA probes (SSH nested PCR-products). Adaptor sequences were removed from the probes by RsaI and SmaI restriction digestion, followed by purification using DNA extraction from agarose gel. Adaptor-free probes were radioactively labeled by random priming using a DNA labeling kit (Gibco BRL Life Technologies) and [$\alpha$-$^{32}$P]-dCTP (Amersham Pharmacia Biotech). All hybridizations were performed at 65° C. under the following conditions: 5×SSC, 5× Denhardt's, 0.5% SDS, 100 µg/ml denatured salmon sperm DNA and an excess of non-radioactive nested primer sequences. Membranes were prehybridized for 5 h prior to hybridization of 5×10$^5$ cpm/ml denatured subtracted cDNA probes for 14 h. Membranes were washed 2 times with 2×SSC and 0.5% SDS at 65° C. for 30 min, followed by 2 washes with 0.2×SSC and 0.5% SDS at 65° C. for 30 min. Autoradiographs were compared and colonies with a strong signal in the plus hybridization (corresponding subtracted SSH library as a probe) and no signal in the minus hybridization (opposite subtracted SSH library as a probe) after background subtraction were identified and selected for sequence analysis and subsequent Northern blot analysis of total RNA from the MDA-MB-231 and MDA2BE5.36 cells.

Isolation of Full-size Human hECRep1a cDNA and Gene

In the SSH analysis, a hECRep1a cDNA fragment of 538 bp was isolated. The full-length hECRep1a cDNA sequence contig of 4,035 nt (GenBank accession number AF458985) was completed by use of cDNA sequence data obtained from isolated phage cDNA clones and by 5' RACE analysis, as outlined further. Supplementary cDNA sequence data were also obtained from expressed sequence tags that were available at that time (EST clones yx82e06, yx43e08, y158e07, zb02a04). Genomic sequence data were initially obtained from a specific genomic PAC clone and later on also from genomic sequence data in the public databases [GenBank accession numbers AC026587 (clone RP11-207G3), AC044815 (clone RP11-196B19), AL157788 (clone RP11-498J9), AL355175 (clone RP11-546C7) and AL355598 (clone RP11-435011)]. The genomic sequence data were used to determine the cDNA sequence at the 5' end by conducting an S1 nuclease protection experiment (see below).

Database Searches:

BLAST searches (Altschul et al., 1990) were performed at GenomeNet in Japan (www blast genome ad jp/) and at the National Center for Biotechnology Information NCBI (http://www.ncbi.nlm.nih.gov/BLAST/). EST clones encoding hECRep1a-specific sequences were ordered from the IMAGE consortium UK-Human Genome Mapping Project (HGMP) Resource Centre (Hinxton).

Isolation of Phage cDNA Clones:

A human fetal kidney 5' stretch cDNA library in vector λDR2 (Clontech) was screened with the $^{32}$P-labeled 538-bp fragment, originally isolated in the differential gene expression analysis. Four plaques were identified upon double screening of approximately 600,000 plaques and converted in vivo to pDR2-derived plasmids according to the manufacturer's instructions. Restriction digestion and sequence analysis revealed that these four clones contain overlapping hECRep1a-specific sequences but none of the clones contained a full-length cDNA insert (FIG. 1).

RACE (Rapid Amplification of cDNA Ends) Experiments:

5' RACE experiments were performed by use of a commercial 5'-RACE system (Gibco BRL) on different human mRNA templates. All RACE products were cloned in pGEM-T or pGEM-Teasy vectors (Promega). Specific though short products were obtained. This is probably due to a suboptimal reverse transcription by virtue of the high GC-content of the 5'-end of the mRNA. Although both the standard protocol and the supplied special protocol for GC-rich sequences were followed, none of these experiments resulted in completion of the 5'-end of the human hECRep1a cDNA sequence.

A 3' RACE experiment was performed using the 3' RACE system of GIBCO BRL. PCR amplification was performed on oligo-dT-primed cDNA, which was synthesized from RNA of the SW480 cell line. The gene-specific primer was 5'-TATGAAATGTCGGCAAAATGACTAT-3' (SEQ ID NO:8) and the nested primer was 5'-GAAGCGAGTTAATATTCTCAGTTG-3' (SEQ ID NO:9). Obtained RACE fragments were purified from agarose gel using the Concert rapid gel extraction kit (Gibco BRL) and then cloned in the pGEM-Teasy vector (Promega).

Isolation and Subcloning of a Genomic PAC Clone:

Superpools and subsequent plate pools from the RPCI1 PAC library (Ioannou and de Jong, 1996) were screened for the hECRep1a sequence by PCR, using primers 5'-TCTTAACCCCAGACCAGAGA-3' (SEQ ID NO:10) and 5'-ATACTCTC CTGGCCTCAAGA-3' (SEQ ID NO:11), and at an annealing temperature of 58° C. A 384-well microtiter plate with plate number #74 scored positive. PCR analysis of the pooled rows and columns of this plate yielded the coordinates of a positive well (16G). Single colonies from this well were grown and checked by PCR for hECRep1-specific sequences. A positive colony was grown and used for DNA isolation with Magnum KB-100 columns (Genome Systems). To subclone this PAC clone DNA, digestions using different restriction enzymes with 6-base recognition sites were performed. To identify fragments that contain hECRep1a gene-specific sequences, the digested DNA was size-fractionized on a 1% FIGE agarose gel (Gibco BRL), transferred to Hybond-N (Amersham Pharmacia Biotech) and hybridized with oligonucleotide 5'-CCGCACAGGGGACACGTGTA-3' (SEQ ID NO:12), that was labeled using [$\gamma$-$^{32}$P]-ATP (Amersham Pharmacia Biotech) and T4 kinase (Gibco BRL). A HindIII 16-kbp DNA fragment, corresponding to a positive signal in the Southern hybridization, was extracted from gel using the Concert Rapid gel extraction kit (Gibco BRL) and cloned into the pGEM-11Zf(+) vector (Promega), which was opened at the HindIII site. The resulting plasmid, designated pGEM11hECRep1aPAC74HindIII, was used for sequencing reactions using hECRep1-specific walking primers.

S1 Nuclease Protection Assay:

To synthesize a hECRep1a-specific genomic template, a 7-kbp HincII fragment was isolated from plasmid pGEM11hECRep1aPAC74HindIII and then digested with XhoI. The generated 1537-bp fragment was size-fractionated on a 1% agarose gel and extracted using the Concert Rapid Gel Extraction kit (Gibco BRL). A $^{32}$P-labeled hECRep1a-specific single-stranded genomic probe of 677 bp was synthesized according to the manufacturer's instructions of the Prime-A-Probe kit (Ambion) using oligonucleotide 5'-CGTCGTCGTCCTCGTCGTAG-3' (SEQ ID NO:13) as primer on the XhoI/HincII fragment as template. The probe was size-fractionized on a denaturing 4% polyacrylamide gel in TBE, followed by elution as described in the protocol. The S1 Nuclease protection assay was performed using the standard procedure of the S1-Assay kit (Ambion). In brief, total RNA derived from SK-BR-3 cells (2.5 µg, 5 µg and 10 µg) was hybridized overnight to $10^5$ cpm $^{32}$P-labeled genomic probe (specific activity $2\times10^3$ cpm/µg) at 42° C., and subsequently treated with 50 U S1 nuclease at 37° C. for 30 min. After precipitation, samples were size-fractionized on a denaturing 5% polyacrylamide gel at 55° C. Gels were dried and detection was done using a Phosphor Imager.

Nucleotide Sequence Analysis:

DNA sequence reactions were performed using the dideoxy chain termination method with fluorescent detection on an ABI-PRISM-377 apparatus (Perkin-Elmer), using plasmid-specific primers and various gene-specific walking primers. All primers were designed using the Oligo 5.0 Primer Analysis software (National Biosciences, Inc.) and were purchased from Gibco BRL. The generated sequences were aligned using STADEN software pregap and gap4.0 (Bonfield et al., 1995).

Identification of Other Nanos-related Genes in Man, Mouse and Rat

Evidence for two more human nanos-related genes was found in the public databases. hECRep1b (or hNanos2) sequences were identified by us as three expressed sequence tags (GenBank accession numbers BI463423, BI826677 and BC042883) and in a genomic clone (GenBank accession number AC008623; clone CTB-14D10). hECRep1c (or hNanos3) sequences were so far only found in one genomic clone (GenBank accession number AC020916; clone CTD-3252C9).

Mouse sequences with high identity to the human hECRep1 genes were found in the public databases and designated by us mECRep1a, -b and -c, respectively (or mNanos-1, -2 and -3). The mECRep1a sequences were identified as a series of EST's, in a plasmid containing a 10-kbp insert of mouse genomic DNA (GenBank accession number AZ425891; clone UUGC1M0206N02) and in the genomic clone RP23-90019 (GenBank accession number AC073823). EST clone mo21e03 (GenBank accession number AI644500) was ordered from the IMAGE consortium UK-Human Genome Mapping Project (HGMP) Resource Centre (Hinxton). The genomic clone UUGC1M0206N02 was ordered from R. B. Weiss at the University of Utah Genome Centre. The mECRep1b sequences were found in one EST sequence (GenBank accession number BE864416) and in a genomic clone (GenBank accession number AC073823; clone RP23-90019). The mECRep1c sequences were found in the genomic clones RP23-298K21 (GenBank accession number AC079515) and RP24-202L5 (GenBank accession number AC122794).

Rat sequences with high identity to the human and mouse h/mECRep1 genes were found in the public databases and designated by us rECRep1a, -b and -c, respectively (or rNanos-1, -2 and -3). The rECRep1a sequences were found in two genomic clones CH230-9N2 and CH230-1M17 (GenBank accession numbers AC125615 and AC096912, respectively). The rECRep1b sequences were found in the two genomic clones CH230-105N7 and CH230-44B8 (GenBank accession numbers AC110846 and AC120692, respectively). The rECRep1c sequences were found in genomic clones CH230-470E24 (GenBank accession number BZ262782), CH230-31N19 (GenBank accession number AC096182) and CH230-250J12 (GenBank accession number AC113860).

Chromosomal Localization

Gene mapping by PCR analysis was performed on the monochromosomal somatic cell hybrid-mapping panel II (Coriell Cell Repositories), utilizing the same hECRep1a-specific primers as for the phage library screening. All cell hybrid templates were diluted to a final DNA concentration of 100 ng/µl, using 1 µl as PCR template.

A more precise mapping of the hECRep1a gene was performed by PCR analysis using the same primer set on the Whole-genome Genebridge 4 Radiation Hybrid DNA panel (Gyapay et al., 1994).

The exact chromosomal localization of hECRep1a was also confirmed and narrowed down in silico at the Human Genome Server of the Ensembl project (at www ensembl. asia org.

Northern Blot Analysis

Total RNA was isolated from various human and mouse cell lines and mouse tissues using the RNeasy kit (Qiagen) according to the manufacturer's instructions. Total RNA (30 µg) was glyoxylated, size-fractionalized on a 1% agarose gel, and transferred to a Hybond-N$^+$ membrane (Amersham Pharmacia Biotech). Hybridizations were performed as described previously (Bussemakers et al., 1991). Probes were radioactively labeled by random priming (RadPrime labeling kit, Gibco BRL). The first hECRep1a-specific probe used was the 538-bp insert of the pGEM-T clone obtained from the PCR-select cDNA subtraction analysis. The human E-cadherin probe used was a 800-bp fragment (encoded by exons 14-16) of the human E-cadherin cDNA. The mECRep1a-specific probe used was the insert of the EST-clone mo21e03. To control for amounts of RNA loaded, a probe specific for GAPDH was used in an additional hybridization on the same blot. Radioactive bands were quantified by the use of a PhosphorImager.

Plasmid Constructs

The eukaryotic expression plasmid pCS3hECRep1a, encoding the complete hECRep1a open reading frame fused to an amino-terminal myc-tag, was constructed by ligation of an SgrAI(blunted)-SalI fragment from plasmid pGEM11hECRep1aPAC74-HindIII into the BglII(blunted)-XhoI cut pCS3 vector (Rupp et al., 1994).

To construct the inducible vector pUHD10.3hECRep1a, a ClaI(blunted)-XbaI fragment from plasmid pCS3hECRep1a was cloned into the EcoRI(blunted)-XbaI cut pUHD10.3 vector (Gossen and Bujard, 1992).

A 682-bp hECRep1a promoter fragment was obtained as an MluI-SgrAI(blunted) fragment from plasmid pGEM11hECRep1aPAC74HindIII and cloned into the MluI-HindIII(blunted) cut pGL3basic vector (Promega). This construct was designated pGL3basic-hECRep1a. Reporter constructs with smaller hECRep1a promoter fragments were constructed by deleting parts in the pGL3basic-hECRep1a plasmid: del1, deletion of MluI-BstEII 165-bp fragment; del2, deletion of MluI-XhoI 366-bp fragment; del3, deletion of MluI-BssHII 471-bp fragment; del4, deletion of BssHII-SacII 186-bp fragment.

The eukaryotic expression plasmid pCS2βctn, encoding full-length human β-catenin, was constructed by ligation of an XbaI(blunted)-SalI β-catenin cDNA fragment from pBAT-βCAT (Hulsken et al., 1994) into the StuI/XhoI-cut pCS2 vector (Rupp et al., 1994).

Cell Culture

The MDCK-Tetoff cell line was obtained from Clontech. This cell line is derived from the Madin Darby Canine Kidney (MDCK) type II epithelial cell line and stably expresses the Tetoff transactivator tTA (Gossen et al., 1995). The cells were maintained in Dulbecco's modified Eagle's medium (DMEM), supplemented with 10% fetal calf serum (FCS), 2 mM L-Gln, 100 U/ml penicillin and 100 µg/ml streptomycin (P/S). The MCF7/AZ cell line (Bracke et al., 1991) is derived from MCF7, a human mammary carcinoma cell line. The cells were maintained in DMEM supplemented with 5% FCS, 2 mM L-Gln, 0.4 mM sodium pyruvate, 6 ng/ml bovine insulin, non-essential amino acids and P/S. Smad4-transfected SW480 cells (clones D1 and D14) and corresponding mock-transfected cells (clones K5 and K6) (Schwarte-Waldhoff et al., 1999) were maintained in DMEM supplemented with 10% FCS and P/S. MDA-MB-231 cells were maintained in L-15 medium (Gibco BRL) supplemented with 10% FCS and P/S. HEK293T cells were maintained in DMEM supplemented with 5% FCS, 5% new born serum (NBS), 2 mM L-Gln, 0.4 mM sodium pyruvate and P/S.

Stable Transfection of Cells

Stable transfection of the E-cadherin-negative MDA-MB-231 cell line was achieved using a standard calcium-phosphate method. At 24 h after seeding, cells grown to subconfluency in a 75-cm² flask were cotransfected with 30 µg of pBATEM2 plasmid, encoding mouse E-cadherin cDNA (Nose et al., 1988), and 3 µg of pPHT plasmid, a derivative of pPNT (Tybulewicz et al., 1991) which confers resistance to hygromycin. Cells were incubated with the transfection mixture for 4 h and seeded 1 over 4 at 24 h after transfection. Stable transfected MDA-MB-231 cells, designated MDA2BE, were selected in 150 U hygromycin-B (Ducheva Biochemie) per ml for 5 weeks. Eighteen clones were isolated with cloning cylinders. Screening for stable clones was performed by immunofluorescence using DECMA-I antibody (Sigma) against mouse E-cadherin. To obtain homogeneous E-cadherin expression, cultures with heterogeneous expression of E-cadherin were subcloned. Therefore, respectively 25, 50, 100, 500, and 5,000 cells of the primary clone were seeded in 75-cm² flasks. For each primary clone, 40 subclones were isolated and screened for homogeneous E-cadherin expression. This yielded clone MDA2BE5.36, which was used for SSH screening.

Stable transfection of the MDCK-Tetoff cell line was achieved using LipofectAMINE PLUS (Life Technologies). At 24 hr after seeding, 2×10⁶ cells per 75-cm² flasks were transfected with 30 µg of linearized pUHD10.3-myc-hECRep1 plasmid or pUHD10.3 plasmid, plus 3 µg of pPHT plasmid. Stable MDCK-Tetoff transfectants, designated MDCK-Tetoff-hECRep1 and MDCK-Tetoff-mock respectively, were selected in 150 U hygromycin B/ml (Duchefa Biochemie) for 2 weeks. Induction of hECRep1 was prevented by adding tetracycline (Tet; 2 µg/ml; Sigma) to the medium. Washing away tetracycline at the time of subcultivation induces expression of myc-tagged hECRep1.

Transient Transfection of Cells

HEK293T cells were transiently transfected by the calcium phosphate method. Transient transfection of MCF7/AZ cells was performed using FuGENE 6 reagent (Roche). Transient transfections of MDA-MB-231 and MDCK-Tetoff-hECRep1a cells were achieved using LipofectAMINE PLUS (Life Technologies).

Promoter Reporter Assays

MDA-MB-231 cells were transiently transfected with luciferase reporter plasmids containing different fragments of the predicted hECRep1a promoter sequence. Approximately 200,000 cells were seeded per 10-cm² well. After a 24-h incubation, 500 ng of each plasmid DNA type was transfected. The medium was refreshed 24 hr after transfection. Three days after transfection, luciferase activity was measured with a Galacto-Star kit (Tropix). Transfection normalization was done by measuring β-galactosidase (Galacto-Star kit; Tropix), encoded by the cotransfected pUT 651 plasmid (Eurogentec).

Immunofluorescence Assays

Methanol fixation and immunofluorescence were achieved by standard procedures (van Hengel et al., 1999). The following antibodies were used: mouse mAb 9E10 against myc-tag (dilution 1/500; (Evan et al., 1985)); rabbit polyclonal Ab against β-catenin (dilution 1/1000; Sigma); mouse mAb pp120 against p120ctn (dilution 1/500, Transduction); mouse mAb PG5.1 against plakoglobin (dilution 1/50; Cymbus); rat mAb DECMA-I against E-cadherin (dilution 1/500; Sigma). Secondary antibodies used were Alexa-488 and Alexa-594 coupled anti-mouse, rat or rabbit Ig (dilution 1/300; Molecular Probes).

Co-immunoprecipitation Assays

Cells were rinsed with PBS and extracted with a lysis buffer, containing 0.5% NP-40, 50 mM Tris-HCl pH 7.4, 150 mM NaCl, 1 µM leupeptin (Sigma), 0.3 pM aprotinin (Sigma) and 5 µM pefablock (Pentapharm Ltd.). Lysates (400 µg of protein) were incubated overnight at 4° C. with 1 µg of the respective antibody. Subsequently, 50 µl of 50% protein-G Sepharose beads (Amersham Pharmacia Biotech) or protein-A Sepharose beads (Amersham Pharmacia Biotech) were added for 2 hours. Adsorbed immunoprecipitates were washed five times with lysis buffer, followed by boiling for 5 min in sample buffer (60 µM Tris-HCl pH 6.8, 1.7% SDS, 6% glycerol, 0.1 M DTT, 0.002% bromophenol blue). Eluted proteins were separated by 10% SDS-PAGE (for detection of β-catenin, p120ctn, plakoglobin and E-cadherin) or 12.5% SDS-PAGE (for detection of myc-hECRep1a), and transferred onto Immobilon-P membranes (Millipore Corp.). After being blocked with 5% nonfat dry milk in TBS containing 0.01% Tween-20, the membranes were incubated with primary antibody. After extensive washing, the membranes were incubated with horseradish peroxidase-conjugated antibodies (dilution 1/3,000; Amersham Pharmacia Biotech) using an enhanced chemiluminescence detection kit (Amersham Pharmacia Biotech) to reveal the proteins.

Cell Aggregation Assays

For a fast cell aggregation assay, single-cell suspensions were prepared according to an E-cadherin-saving procedure using collagenase (Bracke et al., 1993). Cells were incubated for 30 min in an isotonic buffer containing 1.25 mM $Ca^{2+}$ under continuous shaking. E-cadherin could be functionally blocked by treatment with DECMA-I (1/500), starting 30 min before aggregation at 4° C. and continued throughout aggregation at 37° C. Particle diameters were measured in a Coulter particle size counter LS200 (Coulter Electronics Ltd.) at the start of the incubation at 37° C. (N0) and after 30 min of incubation (N30); they were plotted against the volume distribution (expressed as % of the total cell volume).

A slow aggregation assay was performed as previously described (Boterberg et al., 2001). Trypsinized cells were transferred onto a semi-solid agar medium in a 96-well plate. After 1-2 days, aggregation was evaluated with an inverted microscope.

Collagen Invasion Assay

For the collagen invasion assay, cells were seeded on top of a gelified Collagen S (type I, 0.22%) solution (Seromed, Biochrom). Invasion was scored on living cultures using a microscope with computer-controlled stage as described previously by Vakaet et al. (Vakaet Jr et al., 1991).

Example 1

Isolation of the Full-Length hECRep1a cDNA Encoding a Human Nanos-related Protein, and Several Homologs in Man and Mouse E-cadherin-negative Versus-positive Breast Carcinoma Cell Line System A matched cell line couple, basically different in E-cadherin expression, was constructed by stable transfection of the invasive E-cadherin-negative cell line MDA-MB-231 with E-cadherin cDNA. This E-cadherin-positive MDA-MB-231-derivative, designated MDA2BE5.36, shows a restored epithelial phenotype in vitro with respect to strong and homogeneous expression of the E-cadherin/catenin-complex at the cell membrane, epithelioid cell morphology, growth repression, cadherin-dependent cell-cell aggregation, and a shift from a random towards a clustered spatial cell distribution, indicative for decreased invasiveness (Nawrocki-Raby et al., 2001).

Suppression Substractive Hybridization (SHH)

We have sought to identify genes whose expression is modulated by E-cadherin expression. To this end, we conducted a transcriptome analysis for E-cadherin-negative versus E-cadherin-positive cell lines. In an SSH analysis of the closely related breast cancer cell lines MDA-MB-231 and MDA2BE5.36, the mRNA expression of a gene, designated hECRep1a (human E-cadherin repressed clone 1a), was found to be repressed upon E-cadherin expression.

Figure 2:
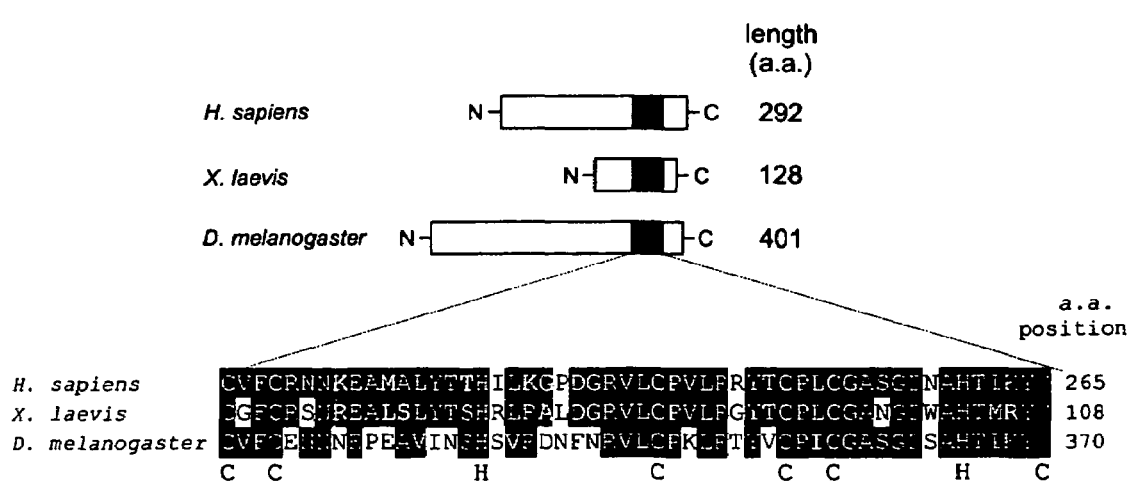
FIG. 2 The human hECRep1a gene encodes a Nanos-like zinc finger protein. (a) The predicted amino acid sequence of hECRep1a protein (SEQ ID NO:2). The characteristic C-terminal zinc finger domain (ZFD) with its conserved CCHC-CCHC residues (boxed) is underlined. This is the only sequence of the hECRep1a protein that shows significant homology to proteins encoded by nanos and nanos-like genes of other organisms. (b) Schematic comparison of the proteins encoded by the human hECRep1a (SEQ ID NO:23), *Xenopus laevis* Xcat-2 (SEQ ID NO:24) (Mosquera et al., 1993) and *Drosophila melanogaster* nanos (SEQ ID NO:25) (Wang and Lehmann, 1991) genes. The black boxes depict the zinc finger domains, for which the amino acid sequences are aligned (Clustal W) at the bottom. Identical and similar amino acids are labeled in black and grey, respectively.
Figure 5:
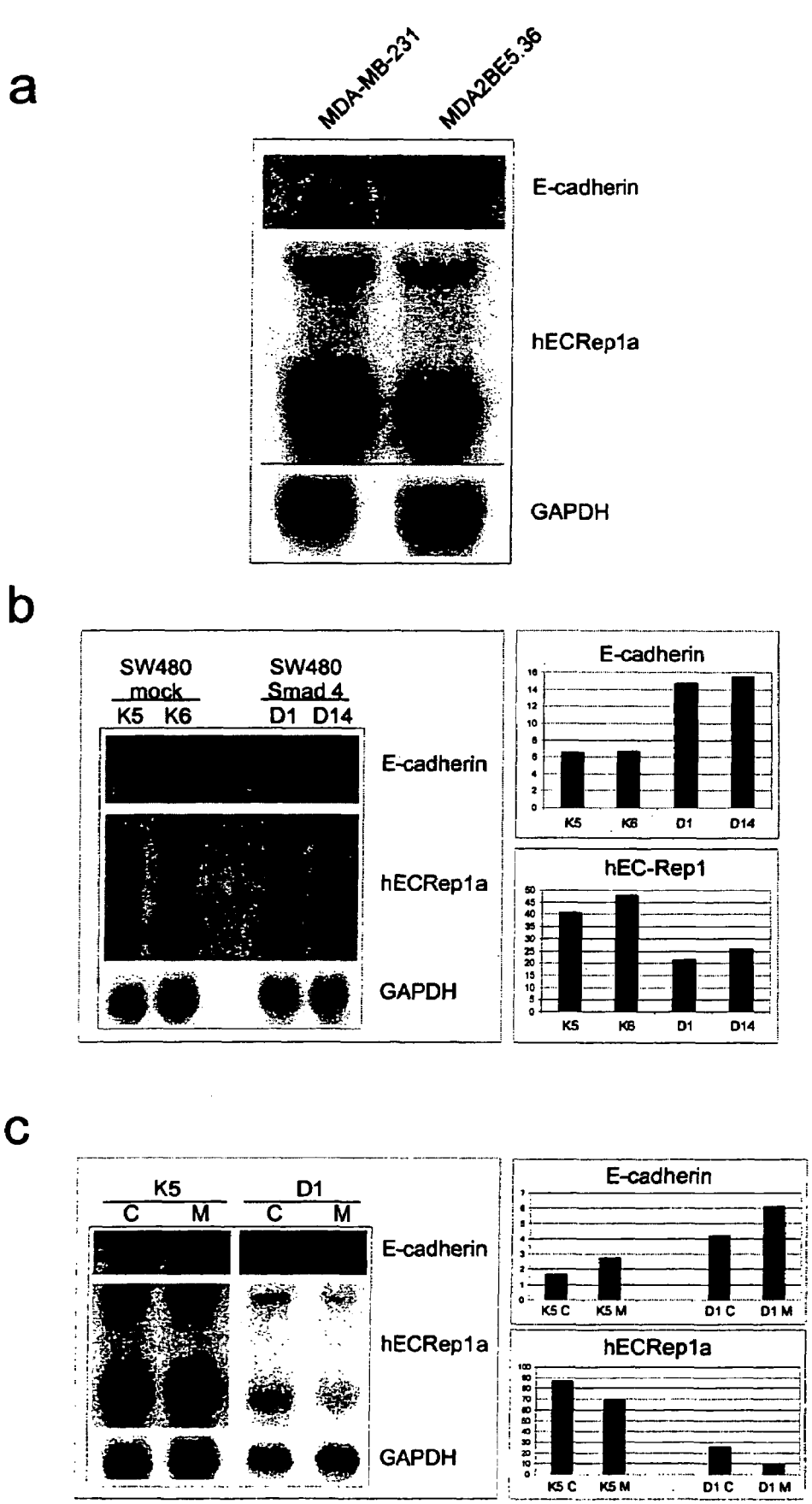
FIG. 5 hECRep1a mRNA expression is down regulated by E-cadherin expression. Results of Northern blot analysis: (a) Expression levels of (mouse) E-cadherin and endogenous human hECRep1a transcripts in MDA-MB-231 cells versus MDA2BE5.36 cells, derived by mouse E-cadherin cDNA transfection of MDA-MB-231 cells. GAPDH hybridization serves as RNA loading control. (b) Expression levels of endogenous hECRep1a and E-cadherin transcripts in mock transfected SW480 control clones (K5 and K6) were compared to Smad4 cDNA transfected SW480 clones (D1 and D14). (c) hECRep1a and E-cadherin expression levels in control K5 and Smad4 transfected D1 SW480 cells that were either grown confluently (C) or as a dense multilayer (M). Graphic bars in (b) and (c) represent mRNA expression levels, normalized to GAPDH expression levels, as measured by quantification of signals on Northern blot.

Isolation of the Full-length hECRep1a cDNA Encoding a Human Nanos-related Protein The cDNA clone, identified in the SSH analysis, comprised an insert of 538 bp that turned out to consist of 3' UTR sequences only (nt 1,662 of the full-size cDNA; FIGS. 1 and 3). This fragment hybridizes to two transcripts when used as a probe in Northern blot analyses (FIGS. 5 and 6a). Both transcripts differ only in the length of their 3' UTR sequences. Indeed, the 4,035-nt full-length cDNA (GenBank accession number AF458985) was determined as described in Materials and Methods, while the second, shorter transcript of 1,810 nt is probably generated by the use of an alternative polyadenylation signal (AAAAAA) at position 1,764 as confirmed by 3' RACE experiments (FIGS. 1 and 3). Alu repeat sequences were recognized in the 3' UTR of the 4,035 transcript between position 3,201 and 3,492. The start codon is predicted to be at position 87 since this is the most upstream ATG codon within the right Kozak environment (Kozak, 1996). The open reading frame starting from this ATG encodes a putative Nanos ortholog of 292 amino acids (FIG. 2a).

Alignment of the predicted hECRep1a amino acid sequence with the sequences of other Nanos-related proteins reveals a high degree of conservation between the $(CCHC)_2$ zinc finger domain nearby the carboxy-terminus. In a span of 52 amino acid residues, ranging from the cysteine residue at position 214 to the cysteine residue at position 265, the predicted hECRep1a protein bears 71.2% identity with the Xcat-2 polypeptide of *Xenopus laevis*, and 61.5% with the Nanos polypeptide of *Drosophila melanogaster* (FIGS. 2b and 4a). Also the spacing in each zinc finger and between both zinc finger domains is highly conserved ($C-X_2-C-X_{12}-H-X_{10}-C-X_7-C-X_2-C-X_7-H-X_4-C$). The restriction of the region of homology to the carboxy-terminal zinc finger domain is not surprising since even Nanos homologues of different Dipteran species (*Drosophila virilis, Musca domestica* and *Chironomus samoensis*), that can functionally substitute for Nanos in *D. melanogaster*, show only strong conservation of the zinc finger domain, while the sequence as well as the length of the amino terminal part of these proteins are poorly conserved (Curtis et al., 1995).

Identification of Other Nanos-related Proteins in Man and Mouse

Two more human Nanos-related amino acid sequences, hECRep1b and -c, could be predicted from human genomic clones of chromosome 19 in the public databases. The hECRep1b protein, as predicted by us on the basis of genomic DNA clone CTB-14D10, comprises 138 amino acids (FIG. 4b). The "*H. sapiens* similar to Xcat-2" protein (accession number XP_064921), that was predicted from NCBI contig NT_011166 by the NCBI Genome Annotation Project, corresponds to but is larger than hECRep1b. The last 136 C-terminal amino acids of this predicted protein of 308 amino acids are identical to the hECRep1b amino acid sequence predicted by us. However, the mRNA annotated by NCBI (accession number XM_064921) does deviate from the EST sequences of hECRep1b in the public database (GenBank accession numbers BI463423, BI826677 and BC042883), while our prediction is in agreement with these EST sequences. Our prediction of the hECRep1c protein of 185 amino acids (FIG. 4b), as based on genomic DNA clone CTD-3252C9, perfectly matches the "*H. sapiens* similar to NANOS" protein (accession number XP_064918) that was predicted from NCBI contig NT_011151 by the NCBI Genome Annotation Project. Alignment of the three human sequences hECRep1a, -b and -c indicates that high identity between these sequences is also restricted to the carboxyterminal zinc finger domains (FIG. 4b). In the amino-terminal part, only short regions of sequence similarity are present.

Three Nanos-related mouse proteins could be predicted from mouse cDNA and genomic DNA sequences in the public databases. These proteins, designated by us as mECRep1a, -b and -c, are most probably the mouse orthologs of the human hECRep1a, -b and -c proteins, respectively (FIG. 4c). The sequence of the mECRep1a protein was predicted on the basis of EST and genomic DNA sequences. EST sequences spanning the entire predicted coding cDNA are available. The predicted mouse protein encompasses 267 amino acid residues showing 83.9% identity with the corresponding human hECRep1a (FIG. 4c). The protein sequence "similar to NANOS" (accession number XP_140766) corresponding to the gene LOC214358, predicted from NCBI contig NW_000148 by the NCBI Genome Annotation Project, overlaps but differs from our prediction of the mECRep1a protein. However, EST sequences confirms our prediction. The mECRep1b protein, as predicted by us on the basis of the genomic DNA clone RP23-90O19, comprises 136 amino acid residues. Deduced amino acids 1 to 121 are in agreement with the partial mECRep1b cDNA sequence of the one available EST-sequence. The entire mouse mECRep1b protein bears 76.5% identity with human hECRep1b (FIG. 4c). The mECRep1c 172 amino acid sequence was predicted from DNA sequence data of clones RP23-298K21 and RP24-202L5, both containing the full-length predicted transcript. Amino acids 1 to 157 perfectly match those deduced from the "similar to nanos homolog" DNA sequence (LOC244551; accession number XM_146605) that was predicted from NCBI contig NW_000349 by the NCBI Genome Annotation Project. The last 15 amino acids, located after the conserved zinc finger motif, are replaced by 21 other amino acids in the NCBI-annotated gene. Alignment of the protein sequence predicted by us to human hECRep1c shows 72.1% identity between these full-length proteins (FIG. 4c).

Three Nanos-related rat proteins could be predicted from rat genomic DNA sequences in the public databases. These proteins, designated by us as rECRep1a, -b and -c, are most probably the rat orthologs of the human and mouse h/mECRep1a, -b and -c proteins, respectively (FIG. 4c). Alignment of the predicted 263 amino acid sequence of rECRep1a to its human and mouse orthologs shows 84.8% identity to the human sequence and 96.2% to the mouse sequence. Analogously, the rECRep1b sequence of 136 amino acids shows 75.0% identity to the human ortholog and 88.2% to the mouse ortholog, while the predicted rECRep1c sequence of 158 amino acids is 78.5% identical to the corresponding human hECRep1c and 96.8% to the mouse mECRep1c sequences.

Example 2

Expression Studies of hECRep1 hECRep1a mRNA Expression is Repressed by E-cadherin Expression

The hECRep1a mRNA was found to be down regulated by E-cadherin expression in a Suppression Subtractive hybridization (SSH)-analysis of the E-cadherin-negative MDA-MB-231 breast cancer cell line versus an E-cadherin-transfected derivative of this cell line, MDA2BE5.36 The effective differential expression of hECRep1a in this cell line couple was confirmed by Northern blot analysis (FIG. 5a). Down-regulation of hECRep1a mRNA expression by E-cadherin expression was further consolidated in SW480 cells, in which E-cadherin expression was induced by stable transfection of Smad4 cDNA (Schwarte-Waldhoff et al., 1999). Equal amounts of total RNA of both Smad4 transfected and mock transfected SW480 cells were analyzed by Northern blotting with an hECRep1a-specific probe (FIG. 5b). Smad4 transfected clones (D1 and D14) show induced E-cadherin mRNA expression and concomitantly reduced hECRep1a mRNA expression compared to E-cadherin-deficient mock-transfected SW480 clones (K5 and K6). Moreover, the inverse correlation between E-cadherin and hECRep1a mRNA expression was further demonstrated in these cells upon culturing them at increasing cell density, which results in induction of E-cadherin expression in both the Smad4 and mock transfected SW480 cells (FIG. 5c).

hECRep1 has a Restricted mRNA Expression Profile

To examine the expression of hECRep1a mRNA in a panel of E-cadherin-negative and -positive cell lines, Northern blot analyses were performed. The hECRep1a-specific 538 bp fragment, isolated in the SSH analysis, was used as a probe. hECRep1a mRNA turned out to be not ubiquitously expressed (FIG. 6a and Table 1) since in the cell line panel analyzed, detection of high hECRep1a expression levels is restricted to the E-cadherin-deficient SW480 colon cancer cell line, SK-BR-3 and MDA-MB-231 breast cancer cell lines, SK-N-AS neuroblastoma cells and WER1-Rb-1 retinoblastoma cells. Moderate expression levels were detected in the A431, MDA2BE5.36 and IMR32 cell lines. All other cell lines tested were low to negative for hECRep1a transcripts. All analyzed hECRep1a-positive cell lines do express both forms of hECRep1a transcripts (FIGS. 5 & 6a).

Expression analysis of the mouse mECRep1a mRNA was performed on RNAs derived from a panel of mouse cell lines and a series of mouse tissues. The insert of EST-clone mo21e03 was used as a probe for Northern blot hybridization. The mouse cell line panel was derived from normal mammary gland cells NMuMG, as described by Vleminckx et al. (1991). Although detectable in both E-cadherin-positive NM-e cells and E-cadherin-negative NM-f cells and in various derivatives thereof, the highest mECRep1a mRNA level was detected in the E-cadherin-negative Ras-transformed NM-f-ras cells (FIG. 6b). Compared to this cell line, mECRep1a mRNA levels are reduced in the E-cadherin-positive NM-e-ras and NM-f-ras-TD-CAM5 (tumor selected E-cadherin transfectant of NM-f-ras) counterparts. Moreover, compared to the levels in the E-cadherin-positive NM-e-ras cell line, mECRep1a mRNA is upregulated in the E-cadherin-deficient NM-e-ras-MAC-pool (containing E-cadherin-specific antisense RNA). mECRep1a mRNA was also detected in the fibroblastic NIH3T3 and in the neural Neuro2A mouse cell lines (data not shown). From all tested mouse tissues, only brain showed detectable mECRep1a mRNA levels (FIG. 6b; right panel).

Based on the availability of EST-sequences in the public databases, hECRep1b (three ESTs) and hECRep1c (no EST at all) show even more restricted expression profiles as compared to hECRep1a (for which some hundred ESTs are in the databases). Moreover, these ratio's between numbers of available ESTs of hECRep1a, -b and -c is also reflected in the corresponding mouse sequences (some hundred ESTs for mECRep1a, only one EST for mECRep1b and no EST at all for mECRep1c).

hECRep1a mRNA Expression is Influenced by TPA Treatment

Treatment of hECRep1a-positive SW480, SK-BR-3 or MDA-MB-231 cells with the phorbol ester 12-O-tetradecanoyl-phorbol-13-acetate alters hECRep1a mRNA expression levels (illustrated in FIG. 7 for SW480 cells). In all tested cells, hECRep1a mRNA levels decrease gradually during the first six hours of TPA treatment, after which hECRep1a mRNA levels are re-induced. At the endpoint of measurement at 24 h of TPA treatment, hECRep1a mRNA levels are even higher as compared to hECRep1a mRNA levels of untreated cells. Although E-cadherin mRNA levels show an opposite alteration profile (increase during the first six hours of treatment followed by a decrease to zero levels at 24 h of TPA treatment) in SW480 cells, the observed changes in hECRep1a mRNA expression levels should be attributed to the TPA treatment rather than to the fluctuations in E-cadherin expression. Indeed, TPA treatment of SK-BR-3 cells, in which E-cadherin cannot be induced since these cells show a homozygous deletion of the E-cadherin gene, has the same effect on hECRep1a mRNA expression levels as observed in the SW480 cells.

hECRep1a mRNA Expression is Increased by Dexamethasone

Figure 8:
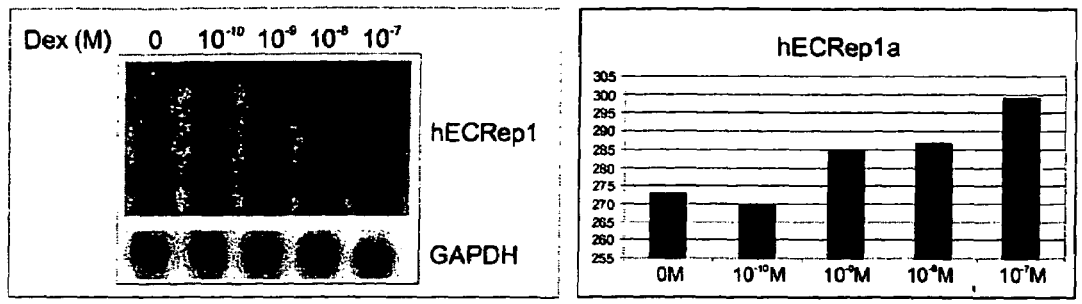
FIG. 8 hECRep1a mRNA expression is increased by dexamethasone (Dex). hECRep1a mRNA expression levels were measured by Northern blot analysis. Subconfluent MDA-MB-231 cells were incubated with different concentrations of Dex as indicated. Cells were lysed after 15 h of incubation. Thirty micrograms of total RNA were loaded per lane. Graphic bars represent mRNA expression levels, obtained from quantification of signals on Northern blot and normalized for RNA loading based on GAPDH mRNA expression levels.

Incubation of MDA-MB-231 cells with the synthetic glucocorticoid dexamethasone (DEX) results in increased hECRep1a mRNA expression levels in a dose-dependent manner (FIG. 8).

Example 3

Human hECRep1a is a Single-exon Gene Mapped to Chromosomal Region 10q25.3

Figure 9:
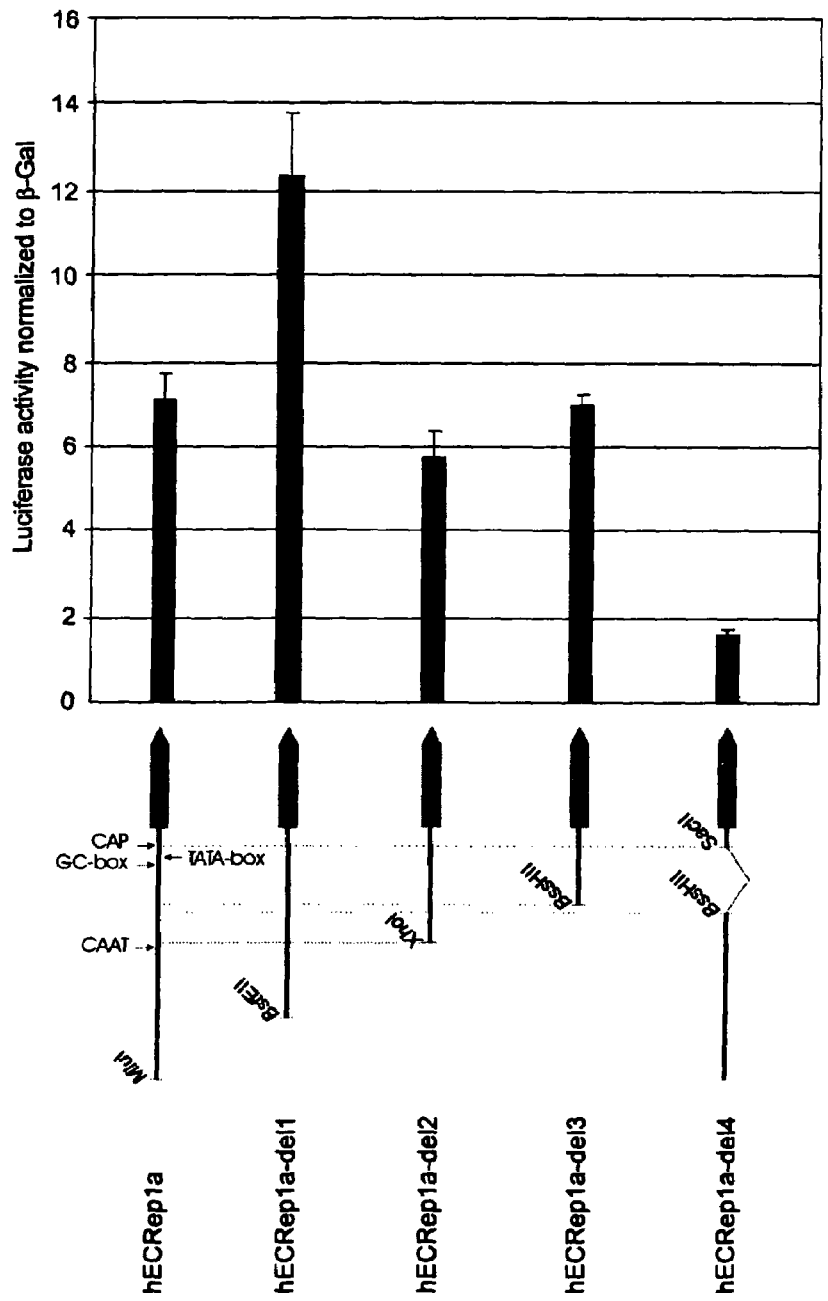
FIG. 9 hECRep1a promoter activity in MDA-MB-231 cells. Cells were transiently transfected with different hECRep1a promoter fragments cloned upstream of the luciferase reporter gene in the pGL3basic vector. Luciferase values representing hECRep1a promoter activity were measured after 3 days and normalized versus β-galactosidase (β-Gal) activities.

To investigate the genomic organization of the hECRep1 gene, a 12,650-nt genomic DNA contig, comprising the hECRep1a cDNA sequence, was subjected to an in silico analysis using the NIX tool at the UK HGMP resource centre (http://www.hgmp.mrc.ac.uk). The genomic contig contained 6,618 nt upstream and 1,997 nt downstream of the defined hECRep1a cDNA sequence. Based on the results of the GENSCAN analysis (Burge and Karlin, 1997), the hECRep1a gene was predicted to be a single-exon gene with an open reading frame as described above. Based on the GRAIL analysis (Xu et al., 1997), promoter elements were recognized including a TATA-box at nt position -33, a GC-box at nt position -54 and a CAAT element at nt position -278 relative to the predicted CAP-structure position (nt position 1 in the cDNA sequence). Reporter plasmids driven by different fragments of the hECRep1a promoter sequences were transiently transfected in the hECRep1a-positive MDA-MB-231 cells (FIG. 9). hECRep1a promoter activity was highest when all three predicted promoter elements (CAAT element, TATA-box and GC-box) were present (pGL3basic-hECRep1a and pGL3basic-hECRep1a-del1). Deletion of either the CAAT-element (pGL3basic-hECRep1-del2 and -del3) or the TATA- and GC-boxes (pGL3basic-hECRep1a-del4) resulted in a marked decrease in promoter activity.

We mapped the human hECRep1a gene to chromosome 10 by PCR performed on a human monochromosomal cell hybrid-mapping panel (FIG. 10a). The hECRep1a-specific fragment was detected only in the lanes containing the positive control and human chromosome 10. Initially, human chromosome 9 scored also positive, but this could not be reproduced in a second experiment. To fine tune the localization of the hECRep1a gene on human chromosome 10, a PCR analysis was performed on the Whole-genome Genebridge 4 Radiation Hybrid DNA panel. Scoring the detection of the hECRep1a-specific fragment at http://menu.hgmp.mrc.ac.uk/RHyME/ lead to the following chromosome-10 microsatellite anchor markers (with their significant LOD-score above 3 between brackets): AFM185yc9 (11.99); AFMa272zd1 (9.23); AFM185xe11 (8.57); AFM331xa9 (5.87); AFM296zg9 (5.46). The hECRep1a gene is therefore most likely mapped between AFM185yc9 and AFM185xe11, corresponding to chromosomal region 10q25.3-10q26.11 on the basis of the Ensembl locations of these markers on the map view of chromosome 10 at http://www.ensembl.org (FIG. 10b). Mapping of the genomic clones that contain hECRep1a sequences on the cytoview of chromosome 10 at this website fixes the chromosomal localization of the human hECRep1a gene to 10q25.3. Moreover, a novel gene was predicted by the Ensembl analysis pipeline at this chromosomal location and annotated as XCAT2 (Enseml ID ENSG00000148922). The corresponding protein sequence is identical to amino acids 214 to 277 of hECRep1a, containing both zinc finger motifs.

We also predict hECRep1b and hECRep1c to be single-exon genes, based on their amino acid sequences that could be predicted directly from the primary genomic DNA sequences. The NCBI-annotated genes LOC126048 (corresponding to hECRep1b) and LOC126041 (corresponding to hECRep1c) were mapped in silico to 19q13.32 and 19p13.13, respectively (world wide web.ncbi.nlm.nih.gov/LocusLink/).

Example 4 hECRep1a Protein is Localized in the Cytoplasmic Compartment

In order to determine the intracellular localization of the hECRep1a protein, immunofluorescence analysis was performed on cells, which exogenously express Myc-tagged hECRep1a, using a mouse anti Myc mAb, 9E10 (Evan et al., 1985).

Figure 11:
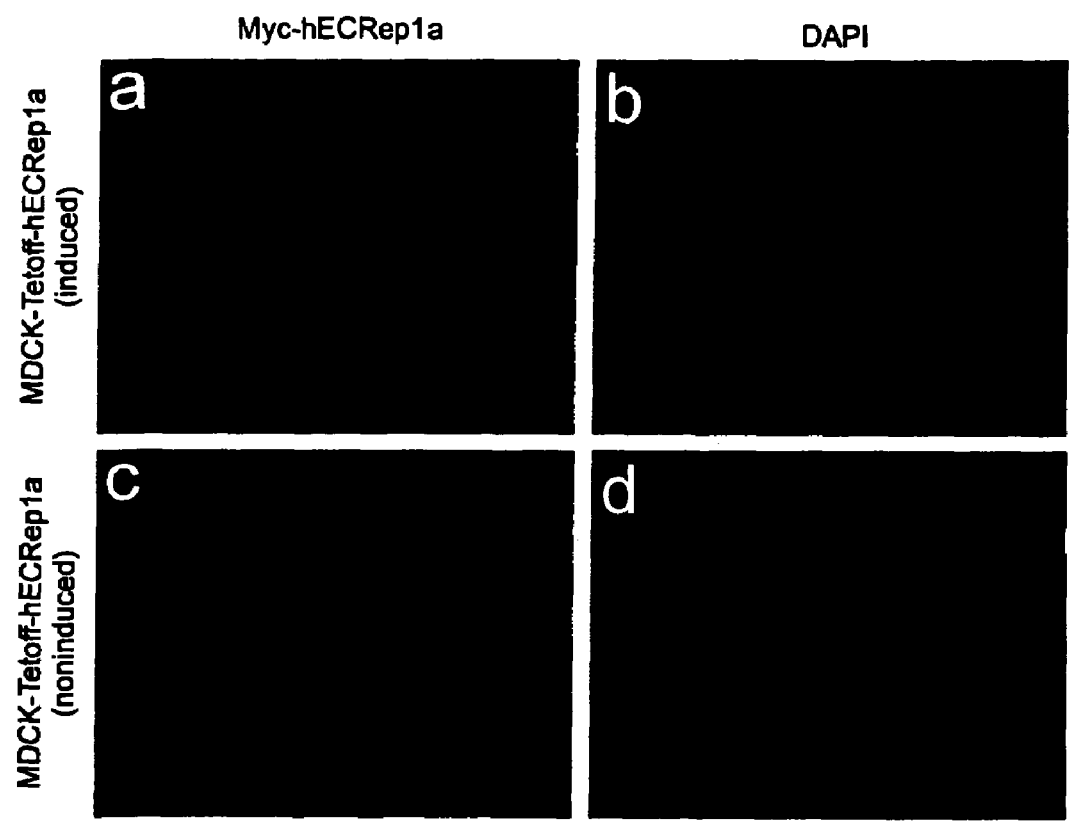
FIG. 11 Immunofluorescence analysis of hECRep1a in MDCK-Tetoff-hECRep1a cells. (a) In induced, tetracycline-free cells, Myc-tagged hECRep1a protein is detected as cytoplasmic dots concentrated around the nucleus. (c) In non-induced, tetracycline-treated cells no Myc-tag-specific staining was detected. (b-d) DAPI was used for nuclear staining.

MDCK-Tetoff cells with high expression of the tTA transactivator were stably transfected with an expression vector for Myc-tagged full-length human hECRep1a under control of a responsive tTA element. To induce hECRep1a, cells were grown without tetracycline (Tet) for 3 days. In these MDCK-Tetoff-hECRep1a cells, induced hECRep1a was detected as cytoplasmic dots concentrated around the nucleus (FIG. 11).

The cytoplasmic staining of hECRep1a was confirmed in MCF7/AZ cells, which were transiently transfected with the pCS3hECRep1a plasmid, encoding Myc-tagged full-length human hECRep1a.

Example 5 hECRep1 Interacts with β-catenin, Plakoglobin and p120ctn

Nanos protein is recruited by Pumilio to the NRE (nanos responsive elements) regulatory elements in the 3' UTR of Hunchback mRNA (Sonoda and Wharton, 1999). Pumilio is a member of a widespread family of sequence-specific RNA binding proteins (Zhang et al., 1997), characterized by eight imperfect repeats of ~36 amino acids (PUM repeats), followed by a C-terminal extension (Wharton et al., 1998). This so-called Puf domain specifies both protein-RNA and protein-protein interactions. Studies of the crystal structure of the Puf domain reveals an extended, rainbow shaped molecule, with tandem helical repeats that bear unexpected resemblance with on the one hand the armadillo (ARM) repeats in β-catenin and importin-α, and on the other hand the HEAT repeats in protein phosphatase 2A (Wang et al., 2001). The Pumilio surface that interacts with Nanos appears to be restricted to a small region that includes the eighth repeat and the C-terminal tail (Edwards et al., 2001).

Based on the Nanos-Pumilio interaction, together with the homology between the zinc finger domain of Nanos and hECRep1a on the one hand, and the similarity between the topology of the Pumilio PUM repeats and β-catenin ARM repeats on the other hand, we investigated the possible interaction between hECRep1a and different human Armadillo proteins. Interaction between hECRep1a and β-catenin, plakoglobin and p120ctn was shown by coimmunoprecipitation either from cell lysates of MDCK-Tetoff-hECRep1a cells with induced hECRep1a expression (-Tet) (FIG. 12a), or from cell lysates of HEK-293T cells transiently cotransfected with pCS3hECRep1a and an expression vector for an armadillo protein (β-catenin or p 120ctn) (FIGS. 12b and c).

Example 6

Role of hECRep1a in Invasion

Conditional hECRep1a Expression Disturbs E-cadherin-dependent Cell-cell Adhesion and Induces Invasion Using a fast aggregation assay in suspension (Bracke et al., 1993), non-induced MDCK-Tetoff-hECRep1a cells (+Tet) showed significant aggregation after 30 min (FIG. 13a), but hECRep1a induction (−Tet) abrogated this normal cell-cell aggregation to an extent similar to that caused by an E-cadherin-blocking antibody, DECMA-I. These results were reproducible for two more dependent MDCK-Tetoff-hECRep1a clones (data not shown).

A comparable effect was observed in a slow aggregation assay (Boterberg et al., 2001). In the case of hECRep1a induction, cell-cell aggregation was abolished at 48 h after seeding MDCK-Tetoff-hECRep1a cells on top of an agar gel, whereas tetracycline-treated non-induced cell aggregates showed obvious compaction by that time (FIG. 13b).

Moreover, invasion into collagen type-I gels was strongly induced by hECRep1a alike the effect induced by the E-cadherin-blocking DECMA-I antibody (FIG. 13c).

TABLE 1 hECRep1a expression in human carcinoma cell lines

| cell line | hECRep1a expression level[a] |
|---|---|
| breast carcinoma | |
| MCF7/AZ | − |
| MCF7/6 | − |
| MDA-MB-134 | − |
| MDA-MB-231 | ++ |
| MDA-MB-435S1 | − |
| MDA2BE5.36 | + |
| MPE600 | − |
| SK-BR-3 | +++ |
| ZR-75-1 | − |
| breast normal | |
| HBL-100 | − |
| colon carcinoma | |
| Colo320DM | − |
| DLD1 | − |
| HCT116 | − |
| HCT8/E8 | − |
| HCT8/R1 | − |
| HT29 | − |
| LOVO | − |
| R2/7 | + |
| SW1116 | − |
| SW480 | +++ |
| SW620 | − |
| epidermoid | |
| A431 | + |
| fibroblast | |
| FS4 | − |
| VA13 | − |
| VA4 | − |
| gastric carcinoma | |
| Kato III | − |
| MKN45 | − |

TABLE 1-continued hECRep1a expression in human carcinoma cell lines

| cell line | hECRep1a expression level[a] |
|---|---|
| glioblastoma | |
| U373MG | − |
| U87MG | − |
| lung carcinoma | |
| GLC34 | − |
| GLC8 | − |
| neuroblastoma | |
| IMR32 | + |
| SK-N-AS | +++ |
| prostate adenocarcinoma | |
| PC3 | + |
| retinoblastoma | |
| WERI-Rb-1 | +++ |
| Y79 | − |
| sarcoma | |
| HOS | + |
| SK-LMS1 | − |
| SW872 | − |
| Thyroid carcinoma | |
| B-CPAP | − |
| FTC133 | − |
| WRO | − |

[a]Endogenous human hECRep1a mRNA levels were measured by Northern blotting. Thirty micrograms of total RNA was loaded per lane. (−) no detectable expression; (+) low expression levels; (++) moderate expression levels; (+++) high expression levels.

REFERENCES

Altschul, S. F., G. Warren, W. Miller, E. W. Myers, and D. J. Lipman. 1990. Basic local alignment search tool. *Journal of Molecular Biology.* 215:403-410.

Anastasiadis, P. Z., S. Y. Moon, M. A. Thoreson, D. J. Mariner, H. C. Crawford, Y. Zheng, and A. B. Reynolds. 2000. Inhibition of RhoA by p120 catenin. *Nature Cell Biology.* 2:637-644.

Anastasiadis, P. Z., and A. B. Reynolds. 2001. Regulation of Rho GTPases by p120-catenin. *Current Opinion in Cell Biology.* 13:604-10.

Becker, K. F., M. J. Atkinson, U. Reich, I. Becker, H. Nekarda, J. R. Siewert, and H. Höfler. 1994. E-cadherin gene mutations provide clues to diffuse type gastric carcinomas. *Cancer Research.* 54:3845-3852.

Behrens, J., M. M. Mareel, F. M. van Roy, and W. Birchmeier. 1989. Dissecting tumor cell invasion: Epithelial cells acquire invasive properties after the loss of uvomorulin-mediated cell-cell adhesion. *Journal of Cell Biology.* 108: 2435-2447.

Behrens, J., J. P. von Kries, M. Kühl, L. Bruhn, D. Wedlich, R. Grosschedl, and W. Birchmeier. 1996. Functional interaction of beta-catenin with the transcription factor LEF-1. *Nature.* 382:638-642.

Berx, G., A.-M. Cleton-Jansen, F. Nollet, W. J. F. de Leeuw, M. J. van de Vijver, C. Cornelisse, and F. van Roy. 1995. E-cadherin is a tumor/invasion suppressor gene mutated in human lobular breast cancers. *EMBO Journal.* 14:6107-6115.

Berx, G., A.-M. Cleton-Jansen, K. Strumane, W. J. F. de Leeuw, F. Nollet, F. M. van Roy, and C. Cornelisse. 1996. E-cadherin is inactivated in a majority of invasive human lobular breast cancers by truncation mutations throughout its extracellular domain. *Oncogene.* 13:1919-1925.

Berx, G., F. Nollet, and F. van Roy. 1998. Dysregulation of the E-cadherin/catenin complex by irreversible mutations in human carcinomas. *Cell Adhesion and Communication.* 6:171-184.

Bonfield, J. K., K. F. Smith, and R. Staden. 1995. A new DNA sequence assembly program. *Nucleic Acids Research.* 23:4992-4999.

Boterberg, T., M. E. Bracke, E. A. Bruyneel, and M. M. Mareel. 2001. Cell aggregation assays. In Metastasis Research Protocols. Vol II: Analysis of Cell Behavior In Vitro and In Vivo. S. A. Brooks and U. Schumacher, editors. Humana Press Inc., Totowa, N.J. 33-45.

Bracke, M. E., N. A. Van Larebeke, B. M. Vyncke, and M. M. Mareel. 1991. Retinoic acid modulates both invasion and plasma membrane ruffling of MCF-7 human mammary carcinoma cells in vitro. *British Journal of Cancer.* 63:867-872.

Bracke, M. E., B. M. Vyncke, E. A. Bruyneel, S. J. Vermeulen, G. K. De Bruyne, N. A. Van Larebeke, K. Vleminckx, F. M. Van Roy, and M. M. Mareel. 1993. Insulin-like growth factor I activates the invasion suppressor function of E-cadherin in MCF-7 human mammary carcinoma cells in vitro. *British Journal of Cancer.* 68:282-289.

Burge, C., and S. Karlin. 1997. Prediction of complete gene structures in human genomic DNA. *Journal of Molecular Biology.* 268:78-94.

Bussemakers, M. J. G., W. J. M. Van de Ven, F. M. J. Debruyne, and J. A. Schalken. 1991. Identification of High Mobility Group Protein I(Y) as potential progression marker for prostate cancer by differential hybridization analysis. *Cancer Research.* 51:606-611.

Curtis, D., J. Apfeld, and R. Lehmann. 1995. nanos is an evolutionarily conserved organizer of anterior-posterior polarity. *Development.* 121:1899-910.

Daniel, J. M., and A. B. Reynolds. 1995. The tyrosine kinase substrate p120(cas) binds directly to E-cadherin but not to the adenomatous polyposis coli protein or alpha-catenin. *Molecular and Cellular Biology.* 15:4819-4824.

Daniel, J. M., and A. B. Reynolds. 1999. The catenin p120 (Ctn) interacts with Kaiso, a novel BTB/POZ domain zinc finger transcription factor. *Molecular and Cellular Biology.* 19:3614-3623.

Edwards, T. A., S. E. Pyle, R. P. Wharton, and A. K. Aggarwal. 2001. Structure of Pumilio reveals similarity between RNA and peptide binding motifs. *Cell.* 105:281-289.

Evan, G. I., G. K. Lewis, G. Ramsay, and J. M. Bishop. 1985. Isolation of monoclonal antibodies specific for human c-myc proto-oncogene product. *Molecular and Cellular Biology.* 5:3610-6.

Frixen, U. H., J. Behrens, M. Sachs, G. Eberle, B. Voss, A. Warda, D. Löchner, and W. Birchmeier. 1991. E-cadherin-mediated cell-cell adhesion prevents invasiveness of human carcinoma cells. *Journal of Cell Biology.* 113:173-185.

Gossen, M., and H. Bujard. 1992. Tight control of gene expression in mammalian cells by tetracycline-responsive promoters. *Proceedings of the National Academy of Sciences of the United States of America.* 89:5547-5551.

Gossen, M., S. Freundlieb, G. Bender, G. Muller, W. Hillen, and H. Bujard. 1995. Transcriptional activation by tetracyclines in mammalian cells. *Science (Washington D.C.).* 268:1766-1769.

Gottardi, C. J., E. Wong, and B. M. Gumbiner. 2001. E-cadherin suppresses cellular transformation by inhibiting beta-catenin signaling in an adhesion-independent manner. *Journal of Cell Biology.* 153:1049-1059.

Gumbiner, B. M. 1997. Carcinogenesis: a balance between beta-catenin and APC. *Current Biology.* 7:R443-R446.

Gyapay, G., J. Morissette, A. Vignal, C. Dib, C. Fizames, P. Millasseau, S. Marc, G. Bernardi, M. Lathrop, and J. Weissenbach. 1994. The 1993-94 genethon human genetic linkage map. *Nature Genetics.* 7:246-339.

Handschuh, G., S. Candidus, B. Luber, U. Reich, C. Schott, S. Oswald, H. Becke, P. Hutzler, W. Birchmeier, H. Hofler, and K. F. Becker. 1999. Tumour-associated E-cadherin mutations alter cellular morphology, decrease cellular adhesion and increase cellular motility. *Oncogene.* 18:4301-4312.

Hu, G., and E. R. Fearon. 1999. Siah-1 N-terminal RING domain is required for proteolysis function, and C-terminal sequences regulate oligomerization and binding to target proteins. *Molecular and Cellular Biology.* 19:724-32.

Hu, G., S. Zhang, M. Vidal, J. LaBaer, T. Xu, and E. R. Fearon. 1997. Mammalian homologs of seven in absentia regulate DCC via the ubiquitin-proteasome pathway. *Genes & Development.* 11:2701-2714.

Huber, O., R. Korn, J. McLaughlin, M. Ohsugi, B. G. Herrmann, and R. Kemler. 1996. Nuclear localization of beta-catenin by interaction with transcription factor LEF-1. *Mechanisms of Development.* 59:3-10.

Hulsken, J., W. Birchmeier, and J. Behrens. 1994. E-cadherin and APC compete for the interaction with beta-catenin and the cytoskeleton. *Journal of Cell Biology.* 127:2061-2069.

Ioannou, P. A., and P. J. de Jong. 1996. Construction of bacterial artificial chromosome libraries using the modified P1 (PAC) system. In Current protocols in human genetics. Dracopoli, editor. John Wiley and Sons, New York.

Jou, T. S., D. B. Stewart, J. Stappert, W. J. Nelson, and J. A. Marrs. 1995. Genetic and biochemical dissection of protein linkages in the cadherin-catenin complex. *Proceedings of the National Academy of Sciences of the United States of America.* 92:5067-5071.

Knudsen, K. A., A. P. Soler, K. R. Johnson, and M. J. Wheelock. 1995. Interaction of alpha-actinin with the cadherin/catenin cell-cell adhesion complex via alpha-catenin. *Journal of Cell Biology.* 130:67-77.

Kozak, M. 1996. Interpreting cDNA sequences: Some insights from studies on translation. *Mammalian Genome.* 7:563-574.

Liu, J., J. Stevens, C. A. Rote, H. J. Yost, Y. X. Hu, K. L. Neufeld, R. L. White, and N. Matsunami. 2001. Siah-1 mediates a novel beta-catenin degradation pathway linking p53 to the adenomatous polyposis coli protein. *Molecular Cell.* 7:927-936.

Matsuzawa, S., and J. C. Reed. 2001. Siah-1, SIP, and Ebi collaborate in a novel pathway for beta-catenin degradation linked to p53 responses. *Molecular Cell.* 7:915-926.

McNeill, H., M. Ozawa, R. Kemler, and W. J. Nelson. 1990. Novel function of the cell adhesion molecule uvomorulin as an inducer of cell surface polarity. *Cell.* 62:309-316.

Miller, J. R., A. M. Hocking, J. D. Brown, and R. T. Moon. 1999. Mechanism and function of signal transduction by the Wnt/beta-catenin and Wnt/Ca2+ pathways. *Oncogene.* 18:7860-7872.

Morin, P. J., A. B. Sparks, V. Korinek, N. Barker, H. Clevers, B. Vogelstein, and K. W. Kinzler. 1997. Activation of beta-catenin-Tcf signalling in colon cancer by mutations in beta-catenin or APC. *Science (Washington D.C.).* 275:1787-1789.

Mosquera, L., C. Forristall, Y. Zhou, and M. L. King. 1993. A mRNA localized to the vegetal cortex of *Xenopus* oocytes encodes a protein with a nanos-like zinc finger domain. *Development*. 117:377-86.

Nawrocki-Raby, B., M. Polette, C. Gilles, C. Clavel, K. Strumane, M. Matos, J.-M. Zahm, F. Van Roy, N. Bonnet, and P. Birembaut. 2001. Quantitative cell dispersion analysis: A new test to measure tumor cell aggressiveness. *International Journal of Cancer*. 92:644-652.

Noren, N. K., B. P. Liu, K. Burridge, and B. Kreft. 2000. p120 catenin regulates the actin cytoskeleton via Rho family GTPases. *Journal of Cell Biology*. 150:567-579.

Nose, A., A. Nagafuchi, and M. Takeichi. 1988. Expressed recombinant cadherins mediate cell sorting in model systems. *Cell*. 54:993-1001.

Orsulic, S., O. Huber, H. Aberle, S. Arnold, and R. Kemler. 1999. E-cadherin binding prevents beta-catenin nuclear localization and beta-catenin/LEF-1-mediated transactivation. *Journal of Cell Science*. 112:1237-1245.

Peifer, M. 1997. Beta-catenin as oncogene: the smoking gun. *Science* (Washington D.C.). 275:1752-1753.

Potter, E., C. Bergwitz, and G. Brabant. 1999. The cadherin-catenin system: Implications for growth and differentiation of endocrine tissues. *Endocrine Reviews*. 20:207-239.

Rimm, D. L., E. R. Koslov, P. Kebriaei, C. D. Cianci, and J. S. Morrow. 1995. Alpha1(E)-catenin is an actin-binding and -bundling protein mediating the attachment of F-actin to the membrane adhesion complex. *Proceedings of the National Academy of Sciences of the United States of America*. 92:8813-8817.

Rubinfeld, B., I. Albert, E. Porfiri, S. Munemitsu, and P. Polakis. 1997. Loss of beta-catenin regulation by the APC tumor suppressor protein correlates with loss of structure due to common somatic mutations of the gene. *Cancer Research*. 57:4624-4630.

Rupp, R. A., L. Snider, and H. Weintraub. 1994. *Xenopus* embryos regulate the nuclear localization of XMyoD. *Genes & Development*. 8:1311-1323.

Sadot, E., I. Simcha, M. Shtutman, A. Ben-Ze'ev, and B. Geiger. 1998. Inhibition of beta-catenin-mediated transactivation by cadherin derivatives. *Proceedings of the National Academy of Sciences of the United States of America*. 95:15339-15344.

Schwarte-Waldhoff, I., S. Klein, S. Blass-Kampmann, A. Hintelmann, C. Eilert, S. Dreschers, H. Kalthoff, S. A. Hahn, and W. Schmiegel. 1999. DPC4/SMAD4 mediated tumor suppression of colon carcinoma cells is associated with reduced urokinase expression. *Oncogene*. 18:3152-3158.

Sonoda, J., and R. P. Wharton. 1999. Recruitment of Nanos to hunchback mRNA by Pumilio. *Genes & Development*. 13:2704-2712.

Stappert, J., and R. Kemler. 1994. A short core region of E-cadherin is essential for catenin binding and is highly phosphorylated. *Cell Adhesion and Communication*. 2:319-327.

Thoreson, M. A., P. Z. Anastasiadis, J. M. Daniel, R. C. Ireton, M. J. Wheelock, K. R. Johnson, D. K. Hummingbird, and A. B. Reynolds. 2000. Selective uncoupling of p120ctn from E-cadherin disrupts strong adhesion. *Journal of Cell Biology*. 148:189-201.

Tybulewicz, V. L. J., C. E. Crawford, P. K. Jackson, R. T. Bronson, and R. C. Mulligan. 1991. Neonatal lethality and lymphopenia in mice with a homozygous disruption of the c-abl proto-oncogene. *Cell*. 65:1153-1163.

Vakaet Jr, L., K. Vleminckx, F. Van Roy, and M. Mareel. 1991. Numerical evaluation of the invasion of closely related cell lines into collagen type I gels. *Invasion & Metastasis*. 11:469-484.

van Hengel, J., P. Vanhoenacker, K. Staes, and F. van Roy. 1999. Nuclear localization of the p120$^{ctn}$ Armadillo-like catenin is counteracted by a nuclear export signal and by E-cadherin expression. *Proceedings of the National Academy of Sciences of the United States of America*. 96:7980-7985.

Vermeulen, S. J., F. Nollet, E. Teugels, K. M. Vennekens, F. Malfait, J. Phillippe, F. Speleman, M. E. Bracke, F. M. van Roy, and M. M. Mareel. 1999. The aE-catenin gene (CT-NNA1) acts as an invasion-suppressor gene in human colon cancer cells. *Oncogene*. 18:905-916.

Vleminckx, K., L. Vakaet Jr, M. Mareel, W. Fiers, and F. van Roy. 1991. Genetic manipulation of E-cadherin expression by epithelial tumor cells reveals an invasion suppressor role. *Cell*. 66:107-119.

Wang, C., and R. Lehmann. 1991. Nanos is the localized posterior determinant in *Drosophila*. *Cell*. 66:637-47.

Wang, X. Q., P. D. Zamore, and T. M. T. Hall. 2001. Crystal structure of a Pumilio homology domain. *Molecular Cell*. 7:855-865.

Wharton, R. P., J. Sonoda, T. Lee, M. Patterson, and Y. Murata. 1998. The Pumilio RNA-binding domain is also a translational regulator. *Molecular Cell*. 1:863-72.

Xu, Y., R. J. Mural, and E. C. Uberbacher. 1997. Inferring gene structures in genomic sequences using pattern recognition and expressed sequence tags. *Proc Int Conf Intell Syst Mol Biol*. 5:344-53.

Zhang, B., M. Gallegos, A. Puoti, E. Durkin, S. Fields, J. Kimble, and M. P. Wickens. 1997. A conserved RNA-binding protein that regulates sexual fates in the *C. elegans* hermaphrodite germ line. *Nature*. 390:477-84.

SEQUENCE LISTING

```
<160> NUMBER OF SEQ ID NOS: 22

<210> SEQ ID NO 1
<211> LENGTH: 4035
<212> TYPE: DNA
<213> ORGANISM: Homo sapiens
<220> FEATURE:
<221> NAME/KEY: CDS
<222> LOCATION: (87)..(965)
<223> OTHER INFORMATION:
<220> FEATURE:
<221> NAME/KEY: misc_feature
<222> LOCATION: (3201)..(3492)
<223> OTHER INFORMATION: ALU
<220> FEATURE:
```

```
<221> NAME/KEY: misc_feature
<222> LOCATION: (2530)..(2530)
<223> OTHER INFORMATION: n can be any nucleotide
<220> FEATURE:
<221> NAME/KEY: misc_feature
<223> OTHER INFORMATION: hECRep1a

<400> SEQUENCE: 1
```

| | | |
|---|---|---|
| ggcaggccgg cgggcaggct cggcgtgtcc cttccgtccg gcccgcgccg gcggcgggga | | 60 |
| ggcggcgcgc ggcccgcagc cgccc atg gag gct ttc ccc tgg gcg ccc cgc<br>              Met Glu Ala Phe Pro Trp Ala Pro Arg<br>               1      5 | | 113 |
| tcg ccc cgc cgc ggc cgc gcc ccc ccg ccc atg gcg ctc gtg ccc agc<br>Ser Pro Arg Arg Gly Arg Ala Pro Pro Pro Met Ala Leu Val Pro Ser<br>10         15         20         25 | | 161 |
| gcc cgc tac gtg agc gcc ccg ggc ccg gcg cac ccg cag ccc ttc agc<br>Ala Arg Tyr Val Ser Ala Pro Gly Pro Ala His Pro Gln Pro Phe Ser<br>        30         35         40 | | 209 |
| tcc tgg aac gac tac ctg ggg ctc gcc acg ctc atc acc aaa gcg gtg<br>Ser Trp Asn Asp Tyr Leu Gly Leu Ala Thr Leu Ile Thr Lys Ala Val<br>         45         50         55 | | 257 |
| gac ggc gag ccg cgc ttc ggc tgc gcc cgc ggt ggg aac ggc ggc ggc<br>Asp Gly Glu Pro Arg Phe Gly Cys Ala Arg Gly Gly Asn Gly Gly Gly<br>       60         65         70 | | 305 |
| ggc tcc ccg ccc tcc tcc tcc tcg tcg tcc tgc tgc tcc ccc cac acg<br>Gly Ser Pro Pro Ser Ser Ser Ser Ser Ser Cys Cys Ser Pro His Thr<br>75         80         85 | | 353 |
| ggg gcc ggg cct ggg gcg ctg ggg ccg gcg ctg ggg ccg ccc gac tac<br>Gly Ala Gly Pro Gly Ala Leu Gly Pro Ala Leu Gly Pro Pro Asp Tyr<br>90         95         100        105 | | 401 |
| gac gag gac gac gac gac gac agc gac gag ccg ggg tcc cgg ggc cgc<br>Asp Glu Asp Asp Asp Asp Asp Ser Asp Glu Pro Gly Ser Arg Gly Arg<br>         110        115        120 | | 449 |
| tac ctg ggg agc gcg ctg gaa ttg cgc gcg ctg gag ctg tgc gcg ggc<br>Tyr Leu Gly Ser Ala Leu Glu Leu Arg Ala Leu Glu Leu Cys Ala Gly<br>          125        130        135 | | 497 |
| ccc gcc gag gcc ggg ctg ctg gag gag cgc ttc gcc gag ctg agc ccg<br>Pro Ala Glu Ala Gly Leu Leu Glu Glu Arg Phe Ala Glu Leu Ser Pro<br>       140         145        150 | | 545 |
| ttc gcg ggt cgt gcc gcc gcc gtg ctg ctg ggc tgc gcg ccc gcc gcc<br>Phe Ala Gly Arg Ala Ala Ala Val Leu Leu Gly Cys Ala Pro Ala Ala<br>     155         160        165 | | 593 |
| gcc gcc gcc gcc acc acc acc agc gag gcg acg ccg cgc gag gag cgg<br>Ala Ala Ala Ala Thr Thr Thr Ser Glu Ala Thr Pro Arg Glu Glu Arg<br>170         175        180        185 | | 641 |
| gcc ccg gcg tgg gcg gcc gag ccc cgg ctg cac gcg gcc tcc ggg gcg<br>Ala Pro Ala Trp Ala Ala Glu Pro Arg Leu His Ala Ala Ser Gly Ala<br>         190        195        200 | | 689 |
| gcg gcc gcc cgg ctg ctg aag ccc gag ctg cag gtg tgc gtg ttc tgc<br>Ala Ala Ala Arg Leu Leu Lys Pro Glu Leu Gln Val Cys Val Phe Cys<br>       205         210        215 | | 737 |
| cgg aac aac aag gag gcg atg gcg ctc tac acc acc cat atc ctc aag<br>Arg Asn Asn Lys Glu Ala Met Ala Leu Tyr Thr Thr His Ile Leu Lys<br>     220         225        230 | | 785 |
| ggc ccc gac ggg cga gtg ctg tgt ccc gtg ctg cgc cgc tac acg tgt<br>Gly Pro Asp Gly Arg Val Leu Cys Pro Val Leu Arg Arg Tyr Thr Cys<br>235         240         245 | | 833 |
| ccc ctg tgc ggc gcc agc ggc gac aac gcg cac acc atc aag tac tgc<br>Pro Leu Cys Gly Ala Ser Gly Asp Asn Ala His Thr Ile Lys Tyr Cys<br>       250         255        260        265 | | 881 |

| | |
|---|---|
| ccg ctc tcc aaa gtg ccg ccg ccg ccc gcc cgc ccg ccc cgc agc<br>Pro Leu Ser Lys Val Pro Pro Pro Pro Ala Arg Pro Pro Pro Arg Ser<br>                    270                      275                      280 | 929 |
| gcc agg gac ggc ccg cct ggc aag aag ctg cgc tga aggcccgggc<br>Ala Arg Asp Gly Pro Pro Gly Lys Lys Leu Arg<br>                    285                      290 | 975 |
| tcccggccgc ccagggtcgc cgccgcccct cgcaccgcta ggtctgcgca ccatctcgcc | 1035 |
| cccgccgtgg ggaggcgtgc ggctcagcgg tcggctcgac atgggacgtc gtcctggtgg | 1095 |
| ttttgaaaa gcagccgacc gtgtggagta cttccgtgct gaacgattgg gactagacgc | 1155 |
| tgaaatcccc atttgtcttc agtttctagt ttgcacatcc agaacggcga aggctgggtg | 1215 |
| tgtattccac taactgaaat atggcaactt agaggcgctg tttatttact gtatacgtcg | 1275 |
| acctatttta gatgcgcatc agtatgaaat tgtctcaatc ttggatgttt cattttatga | 1335 |
| atggaggcac tttactaggt ctagaatatt ttttaaaag cctctgaact gagcttaaaa | 1395 |
| ctggcgattt tatgaaatgt cggcaaaatg actattttat tgtttgaagc gagttaatat | 1455 |
| tctcagttgt ctttaaaaat cagttactct aattccaggt gaagcaagcc gctggtagca | 1515 |
| tcacccttat gagaagtgaa ggttttgtaa actttccagt attaatttgg gcgggtattc | 1575 |
| cccgcttgtg gcttgtttct gtcctagctg gaggtgtaaa atgcacaatg tgtagcaggt | 1635 |
| agaatacagc tccttatcgt tctatgtacc aggtatttta ttactgaact agcaactagc | 1695 |
| cttttccacc tttaaaagtt gtgccaagtc ataatcatat tgtgtataac ttggaaatgg | 1755 |
| tgctgtttaa aaaaattgtg tatttataca gtaacagtat gaattcatta atctcacctg | 1815 |
| taactttcct acttggcctt ttctctacac actcaccctc ttccagttct ttaaaaacgt | 1875 |
| ttatgatatt aagatcaaag ggaggaaggg aagacagcag tattaattca ccctagatta | 1935 |
| ctcaatttca gggttcctag tggaggaaag cccattccag ctgttgcctg tcaaacaaat | 1995 |
| agaagatgga tctctagctc tgagctattc gtgtattaac tcgtattcaa gaaggttcca | 2055 |
| ccgtgggctg cgtctgactt aatacaggc agtgctcaaa ctagaataag cactaattaa | 2115 |
| aggaattgtt gggggtcctt catgtgttcc cactcctact ggaagaccca tgtcggtttc | 2175 |
| cggaacccca ccagtttacc cataagcaag actaaacctg atccttgggc aaaagttcct | 2235 |
| aaccccctact ttaccctccc accctcactt taaatccac catactgaat gccacactat | 2295 |
| ggaatgcagc tacctgccaa gcaaggcaat agaaggcaaa aatggaagt gaattaagat | 2355 |
| gaactcatct gaaatacaca aatgcattac tatctgaaga taccagcaag agtttagtct | 2415 |
| acgtgtataa ggctcccagt aggatttagc taggctacta gaagttagac tgctttcgca | 2475 |
| ttaaacagct aacttcattc acagcaaatt gacttaatca gaacctttat tttgnaaggt | 2535 |
| gtgttagaag gatgggggtc catagctgtc tttttggtga agaaaaggt gcatttcaag | 2595 |
| aacttggggg gcaggaggaa agcacaatgt ttcttagcca ggaaagacaa ataatccaac | 2655 |
| gctgctagtc ttaaccccag accagagaga actgcagatc tgactgggcc taaattaagt | 2715 |
| agcttaatga aaccatgtaa ttacttgttc tcctttcttt tgctatagaa aatctaccag | 2775 |
| tttaaatgag cttcacccttc tgggtgaagt ttctaaggtc aacatgaatc ctcttacctc | 2835 |
| tctcactgct cgtgttctgc cttttcaaaa ggaccactat gaacagatca gcgcattctc | 2895 |
| taggccaaaa gggctagcca ggtggcaaga tcaatttagc tactttgtat tttcagagtc | 2955 |
| aaattacaga cggttccaa aggtcttgag catgggcctt tggcatagcc tcaatatatg | 3015 |
| ggagtcactg tgatgagatg tgcctaatgt taatttgata ttctgacatt gctactatttt | 3075 |
| taccagaact aagaacatat tgagctggag cttcttgagg gcaggagagt attggaaaag | 3135 |

-continued

```
gaatccagaa gaccctctcc actactcagg cagccactat tcatctatttt ttaaagtacc    3195 ccattttcag gccgggtgtg gtggctcatg cctgtaatcc cagcactttg ggaggcgagg    3255
cgggggtgga tcacaaggtc aggagaccag cctggccaac atggcgaagc cccgtctcta    3315
ctaaaaatac aaaaattagc cgggtggtgt ggtgggcgcc tgtaatccca gctcctcagg    3375
aggctgaggc aggagaattg cttgaaacca ggaggcggag gttgcagtga gcccagatca    3435
cgccactgca ctccagcctg gcaacagag cgactctgta tccaaaaaaa aaaaaaagta     3495
ccccatgttc agcccctgtg ccaaatttgc ctaggttttc cagctgacaa tgaatactgg    3555
gagttaaaac gcagagtatt actatagtta attttctagg gttctcttat gaaaagtata    3615
tgtaaacaca ttcatttaaa aatccttgga actcaatgtg gaactttaaa cattttgcaa    3675
aattacattt agagaaaccc aattttttcaa agtttaagaa atatacaaag tatgacaaaa    3735
ttatcttcat aagaacatgc tgcatacttg cctagtagca aaacaataca gggaagagtc    3795
aaaagggctt ctccaactgt agaggtacag attgtcttaa cctgttcttt tctgtacaga    3855
cttaaaattt ctagtggctt ttatttttct ttgtatttta attttcctac aaagtccttt    3915
ttggaagttg cagaattatt agctttgatg agaacaactt ttgtcataga tttgatttat    3975
taaaccaaaa ttatacatat taaaattata tcacaaatat aaaaaaaaaa aaaaaaaaa    4035
```

<210> SEQ ID NO 2
<211> LENGTH: 292
<212> TYPE: PRT
<213> ORGANISM: Homo sapiens
<220> FEATURE:
<221> NAME/KEY: misc_feature
<222> LOCATION: (3201)..(3492)
<223> OTHER INFORMATION: ALU
<220> FEATURE:
<221> NAME/KEY: misc_feature
<222> LOCATION: (2530)..(2530)
<223> OTHER INFORMATION: n can be any nucleotide
<220> FEATURE:
<221> NAME/KEY: misc_feature
<223> OTHER INFORMATION: hECRep1a

<400> SEQUENCE: 2

```
Met Glu Ala Phe Pro Trp Ala Pro Arg Ser Pro Arg Gly Arg Ala
1               5                  10                  15

Pro Pro Pro Met Ala Leu Val Pro Ser Ala Arg Tyr Val Ser Ala Pro
            20                  25                  30

Gly Pro Ala His Pro Gln Pro Phe Ser Ser Trp Asn Asp Tyr Leu Gly
        35                  40                  45

Leu Ala Thr Leu Ile Thr Lys Ala Val Asp Gly Glu Pro Arg Phe Gly
    50                  55                  60

Cys Ala Arg Gly Gly Asn Gly Gly Gly Ser Pro Pro Ser Ser
65                  70                  75                  80

Ser Ser Ser Cys Cys Ser Pro His Thr Gly Ala Gly Pro Ala Leu
                85                  90                  95

Gly Pro Ala Leu Gly Pro Pro Asp Tyr Asp Glu Asp Asp Asp Asp
            100                 105                 110

Ser Asp Glu Pro Gly Ser Arg Gly Arg Tyr Leu Gly Ser Ala Leu Glu
        115                 120                 125

Leu Arg Ala Leu Glu Leu Cys Ala Gly Pro Ala Glu Ala Gly Leu Leu
    130                 135                 140

Glu Glu Arg Phe Ala Glu Leu Ser Pro Phe Ala Gly Arg Ala Ala Ala
145                 150                 155                 160
```

Val Leu Leu Gly Cys Ala Pro Ala Ala Ala Ala Thr Thr Thr
            165                 170             175

Ser Glu Ala Thr Pro Arg Glu Arg Ala Pro Ala Trp Ala Ala Glu
            180                 185             190

Pro Arg Leu His Ala Ala Ser Gly Ala Ala Ala Arg Leu Leu Lys
            195                 200             205

Pro Glu Leu Gln Val Cys Val Phe Cys Arg Asn Asn Lys Glu Ala Met
            210                 215             220

Ala Leu Tyr Thr Thr His Ile Leu Lys Gly Pro Asp Gly Arg Val Leu
225             230                 235             240

Cys Pro Val Leu Arg Arg Tyr Thr Cys Pro Leu Cys Gly Ala Ser Gly
            245                 250             255

Asp Asn Ala His Thr Ile Lys Tyr Cys Pro Leu Ser Lys Val Pro Pro
            260                 265             270

Pro Pro Ala Arg Pro Pro Arg Ser Ala Arg Asp Gly Pro Pro Gly
            275                 280             285

Lys Lys Leu Arg
    290

<210> SEQ ID NO 3
<211> LENGTH: 417
<212> TYPE: DNA
<213> ORGANISM: Homo sapiens
<220> FEATURE:
<221> NAME/KEY: CDS
<222> LOCATION: (1)..(417)
<223> OTHER INFORMATION:
<220> FEATURE:
<221> NAME/KEY: misc_feature
<223> OTHER INFORMATION: hECRep1b

<400> SEQUENCE: 3

| atg cag ctg cca ccc ttc gac atg tgg aag gac tac ttc aac ctg agc | 48 |
|---|---|
| Met Gln Leu Pro Pro Phe Asp Met Trp Lys Asp Tyr Phe Asn Leu Ser | |
| 1               5                   10                  15 | |

| cag gtg gtg tgg gcg ctg atc gca agt cgg ggt caa agg ctg gag acc | 96 |
|---|---|
| Gln Val Val Trp Ala Leu Ile Ala Ser Arg Gly Gln Arg Leu Glu Thr | |
|             20                  25                  30 | |

| caa gag att gag gag cca agt ccc ggg cct ccg ctg ggg cag gat cag | 144 |
|---|---|
| Gln Glu Ile Glu Glu Pro Ser Pro Gly Pro Pro Leu Gly Gln Asp Gln | |
|         35                  40                  45 | |

| ggg ctg ggg gcg cca ggg gcc aac ggg ggc ctg ggg acc ctg tgc aac | 192 |
|---|---|
| Gly Leu Gly Ala Pro Gly Ala Asn Gly Gly Leu Gly Thr Leu Cys Asn | |
| 50                  55                  60 | |

| ttc tgc aag cac aac ggg gag tcc cgc cac gtc tac tcc tca cac cag | 240 |
|---|---|
| Phe Cys Lys His Asn Gly Glu Ser Arg His Val Tyr Ser Ser His Gln | |
| 65              70                  75                  80 | |

| ctg aag aca ccg gat ggc gtg gtg gtg tgt ccc atc ctg agg cac tac | 288 |
|---|---|
| Leu Lys Thr Pro Asp Gly Val Val Val Cys Pro Ile Leu Arg His Tyr | |
|             85                  90                  95 | |

| gtg tgt ccc gtg tgc ggg gcc acc ggt gac cag gcc cat acg ctc aag | 336 |
|---|---|
| Val Cys Pro Val Cys Gly Ala Thr Gly Asp Gln Ala His Thr Leu Lys | |
|         100                 105                 110 | |

| tac tgc ccg ctt aac ggt ggc cag cag tcc ctc tac cgc cgc agc ggg | 384 |
|---|---|
| Tyr Cys Pro Leu Asn Gly Gly Gln Gln Ser Leu Tyr Arg Arg Ser Gly | |
|         115                 120                 125 | |

| cgc aac tcg gcc gga cgc agg gtc aag cgc tga | 417 |
|---|---|
| Arg Asn Ser Ala Gly Arg Arg Val Lys Arg | |
|     130                 135 | |

<210> SEQ ID NO 4
<211> LENGTH: 138
<212> TYPE: PRT
<213> ORGANISM: Homo sapiens
<220> FEATURE:
<221> NAME/KEY: misc_feature
<223> OTHER INFORMATION: hECRep1b

<400> SEQUENCE: 4

Met Gln Leu Pro Pro Phe Asp Met Trp Lys Asp Tyr Phe Asn Leu Ser
1               5                   10                  15

Gln Val Val Trp Ala Leu Ile Ala Ser Arg Gly Gln Arg Leu Glu Thr
            20                  25                  30

Gln Glu Ile Glu Glu Pro Ser Pro Gly Pro Pro Leu Gly Gln Asp Gln
        35                  40                  45

Gly Leu Gly Ala Pro Gly Ala Asn Gly Gly Leu Gly Thr Leu Cys Asn
    50                  55                  60

Phe Cys Lys His Asn Gly Glu Ser Arg His Val Tyr Ser Ser His Gln
65                  70                  75                  80

Leu Lys Thr Pro Asp Gly Val Val Val Cys Pro Ile Leu Arg His Tyr
                85                  90                  95

Val Cys Pro Val Cys Gly Ala Thr Gly Asp Gln Ala His Thr Leu Lys
            100                 105                 110

Tyr Cys Pro Leu Asn Gly Gly Gln Gln Ser Leu Tyr Arg Arg Ser Gly
        115                 120                 125

Arg Asn Ser Ala Gly Arg Arg Val Lys Arg
    130                 135

<210> SEQ ID NO 5
<211> LENGTH: 558
<212> TYPE: DNA
<213> ORGANISM: Homo sapiens
<220> FEATURE:
<221> NAME/KEY: CDS
<222> LOCATION: (1)..(558)
<223> OTHER INFORMATION:
<220> FEATURE:
<221> NAME/KEY: misc_feature
<223> OTHER INFORMATION: hECRep1c

<400> SEQUENCE: 5 atg ggg acc ttt gac ctg tgg aca gat tac ctg ggt ttg gca cac ctg      48
Met Gly Thr Phe Asp Leu Trp Thr Asp Tyr Leu Gly Leu Ala His Leu
1               5                   10                  15 gtt agg gct ctg agt ggg aaa gag ggt cct gaa acc agg ctg agc ccc      96
Val Arg Ala Leu Ser Gly Lys Glu Gly Pro Glu Thr Arg Leu Ser Pro
            20                  25                  30 cag cca gag cca gag cca atg ctg gag ccg gtg tca gcc ctg gag ccg     144
Gln Pro Glu Pro Glu Pro Met Leu Glu Pro Val Ser Ala Leu Glu Pro
        35                  40                  45 atg cca gcg ccg gag tcg gtg cca gtg ccg gga ccc aag gat cag aag     192
Met Pro Ala Pro Glu Ser Val Pro Val Pro Gly Pro Lys Asp Gln Lys
    50                  55                  60 cgc agc ctg gag tcc tcg cca gct ccc gaa cgc ctg tgc tct ttc tgc     240
Arg Ser Leu Glu Ser Ser Pro Ala Pro Glu Arg Leu Cys Ser Phe Cys
65                  70                  75                  80 aaa cac aac ggc gag tcc cgg gcc atc tac cag tcc cac gtg ctg aag     288
Lys His Asn Gly Glu Ser Arg Ala Ile Tyr Gln Ser His Val Leu Lys
                85                  90                  95 gac gag gct ggc agg gtg ctg tgt ccc atc ctg cgg gac tac gtg tgt     336
Asp Glu Ala Gly Arg Val Leu Cys Pro Ile Leu Arg Asp Tyr Val Cys -continued

```
              100                 105                 110
ccc cag tgc ggc gcc aca cgt gag cgc gcc cac acc cga cgc ttc tgc      384
Pro Gln Cys Gly Ala Thr Arg Glu Arg Ala His Thr Arg Arg Phe Cys
        115                 120                 125 cca ctt act ggc cag ggc tac acc tcc gtc tac agc cac acc acc cga      432
Pro Leu Thr Gly Gln Gly Tyr Thr Ser Val Tyr Ser His Thr Thr Arg
    130                 135                 140 aac tcg gca ggc aag aag ctg gtc cgg cct gac aag gcg aag aca cag      480
Asn Ser Ala Gly Lys Lys Leu Val Arg Pro Asp Lys Ala Lys Thr Gln
145                 150                 155                 160 gac aca ggc cac cgc cga gga gga gga gga gca ggt gcc tgc aca          528
Asp Thr Gly His Arg Arg Gly Gly Gly Gly Ala Gly Ala Cys Thr
                165                 170                 175 ggt ggc tgg ggg gga cct gtc cga ggg tag                              558
Gly Gly Trp Gly Gly Pro Val Arg Gly
            180                 185
```

<210> SEQ ID NO 6
<211> LENGTH: 185
<212> TYPE: PRT
<213> ORGANISM: Homo sapiens
<220> FEATURE:
<221> NAME/KEY: misc_feature
<223> OTHER INFORMATION: hECRep1c

<400> SEQUENCE: 6

```
Met Gly Thr Phe Asp Leu Trp Thr Asp Tyr Leu Gly Leu Ala His Leu
1               5                   10                  15

Val Arg Ala Leu Ser Gly Lys Glu Gly Pro Glu Thr Arg Leu Ser Pro
                20                  25                  30

Gln Pro Glu Pro Glu Pro Met Leu Glu Pro Val Ser Ala Leu Glu Pro
            35                  40                  45

Met Pro Ala Pro Glu Ser Val Pro Val Pro Gly Pro Lys Asp Gln Lys
        50                  55                  60

Arg Ser Leu Glu Ser Ser Pro Ala Pro Glu Arg Leu Cys Ser Phe Cys
65                  70                  75                  80

Lys His Asn Gly Glu Ser Arg Ala Ile Tyr Gln Ser His Val Leu Lys
                85                  90                  95

Asp Glu Ala Gly Arg Val Leu Cys Pro Ile Leu Arg Asp Tyr Val Cys
            100                 105                 110

Pro Gln Cys Gly Ala Thr Arg Glu Arg Ala His Thr Arg Arg Phe Cys
        115                 120                 125

Pro Leu Thr Gly Gln Gly Tyr Thr Ser Val Tyr Ser His Thr Thr Arg
    130                 135                 140

Asn Ser Ala Gly Lys Lys Leu Val Arg Pro Asp Lys Ala Lys Thr Gln
145                 150                 155                 160

Asp Thr Gly His Arg Arg Gly Gly Gly Gly Ala Gly Ala Cys Thr
                165                 170                 175

Gly Gly Trp Gly Gly Pro Val Arg Gly
            180                 185
```

<210> SEQ ID NO 7
<211> LENGTH: 26
<212> TYPE: PRT
<213> ORGANISM: Artificial Sequence
<220> FEATURE:
<223> OTHER INFORMATION: hECRep homologue
<220> FEATURE:
<221> NAME/KEY: MISC_FEATURE
<222> LOCATION: (3)..(3)

```
<223> OTHER INFORMATION: X can be any amino acid residue
<220> FEATURE:
<221> NAME/KEY: MISC_FEATURE
<222> LOCATION: (6)..(6)
<223> OTHER INFORMATION: X can be any amino acid residue
<220> FEATURE:
<221> NAME/KEY: MISC_FEATURE
<222> LOCATION: (8)..(8)
<223> OTHER INFORMATION: X can be any amino acid residue
<220> FEATURE:
<221> NAME/KEY: MISC_FEATURE
<222> LOCATION: (11)..(11)
<223> OTHER INFORMATION: X can be any amino acid residue
<220> FEATURE:
<221> NAME/KEY: MISC_FEATURE
<222> LOCATION: (15)..(18)
<223> OTHER INFORMATION: X can be any amino acid residue
<220> FEATURE:
<221> NAME/KEY: MISC_FEATURE
<222> LOCATION: (22)..(24)
<223> OTHER INFORMATION: X can be any amino acid residue

<400> SEQUENCE: 7

Cys Pro Xaa Leu Arg Xaa Tyr Xaa Cys Pro Xaa Cys Gly Ala Xaa Xaa
1               5                   10                  15

Xaa Xaa Ala His Thr Xaa Xaa Xaa Cys Pro
            20                  25

<210> SEQ ID NO 8
<211> LENGTH: 25
<212> TYPE: DNA
<213> ORGANISM: Artificial Sequence
<220> FEATURE:
<223> OTHER INFORMATION: gene-specific primer

<400> SEQUENCE: 8
tatgaaatgt cggcaaaatg actat                                     25

<210> SEQ ID NO 9
<211> LENGTH: 24
<212> TYPE: DNA
<213> ORGANISM: Artificial Sequence
<220> FEATURE:
<223> OTHER INFORMATION: nested primer

<400> SEQUENCE: 9
gaagcgagtt aatattctca gttg                                      24

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tcttaacccc agaccagaga                                           20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
atactctcct ggcctcaaga                                           20
```

```
<210> SEQ ID NO 12
<211> LENGTH: 20
<212> TYPE: DNA
<213> ORGANISM: Artificial Sequence
<220> FEATURE:
<223> OTHER INFORMATION: oligonucleotide

<400> SEQUENCE: 12
ccgcacaggg gacacgtgta                                                 20

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
cgtcgtcgtc ctcgtcgtag                                                 20

<210> SEQ ID NO 14
<211> LENGTH: 52
<212> TYPE: PRT
<213> ORGANISM: Artificial Sequence
<220> FEATURE:
<223> OTHER INFORMATION: zinc finger homologue
<220> FEATURE:
<221> NAME/KEY: MISC_FEATURE
<222> LOCATION: (2)..(3)
<223> OTHER INFORMATION: X can be any amino acid residue
<220> FEATURE:
<221> NAME/KEY: MISC_FEATURE
<222> LOCATION: (5)..(16)
<223> OTHER INFORMATION: X can be any amino acid residue
<220> FEATURE:
<221> NAME/KEY: MISC_FEATURE
<222> LOCATION: (18)..(27)
<223> OTHER INFORMATION: X can be any amino acid residue
<220> FEATURE:
<221> NAME/KEY: MISC_FEATURE
<222> LOCATION: (29)..(35)
<223> OTHER INFORMATION: X can be any amino acid residue
<220> FEATURE:
<221> NAME/KEY: MISC_FEATURE
<222> LOCATION: (37)..(38)
<223> OTHER INFORMATION: X can be any amino acid residue
<220> FEATURE:
<221> NAME/KEY: MISC_FEATURE
<222> LOCATION: (40)..(46)
<223> OTHER INFORMATION: X can be any amino acid residue
<220> FEATURE:
<221> NAME/KEY: MISC_FEATURE
<222> LOCATION: (48)..(51)
<223> OTHER INFORMATION: X can be any amino acid residue

<400> SEQUENCE: 14

Cys Xaa Xaa Cys Xaa Xaa Xaa Xaa Xaa Xaa Xaa Xaa Xaa Xaa Xaa Xaa
1               5                   10                  15

His Xaa Xaa Xaa Xaa Xaa Xaa Xaa Xaa Xaa Xaa Cys Xaa Xaa Xaa Xaa
            20                  25                  30

Xaa Xaa Xaa Cys Xaa Xaa Cys Xaa Xaa Xaa Xaa Xaa Xaa Xaa His Xaa
        35                  40                  45

Xaa Xaa Xaa Cys
    50

<210> SEQ ID NO 15
<211> LENGTH: 128
<212> TYPE: PRT
<213> ORGANISM: Xenopus laevis
```

```
<400> SEQUENCE: 15

Met Asp Gly Gly Leu Cys Phe Asp Ser Trp Ser Asp Tyr Leu Gly Leu
1               5                   10                  15

Ser Ser Leu Ile Ser Arg Gly Leu Gln Pro Gln Arg Glu Gly Glu Arg
            20                  25                  30

Pro Arg Trp Asp Val Leu Ser Pro Ala Ser Ala Glu Pro Leu Pro Ser
        35                  40                  45

Asn Glu Ser Val Gly His Lys Gly Cys Gly Phe Cys Arg Ser Asn Arg
    50                  55                  60

Glu Ala Leu Ser Leu Tyr Thr Ser His Arg Leu Arg Ala Leu Asp Gly
65                  70                  75                  80

Arg Val Leu Cys Pro Val Leu Arg Gly Tyr Thr Cys Pro Leu Cys Gly
                85                  90                  95

Ala Asn Gly Asp Trp Ala His Thr Met Arg Tyr Cys Pro Leu Arg Arg
            100                 105                 110

Leu Leu Arg Asp Pro Gln Ser Asn Ser Asn Pro Lys Leu Arg His
        115                 120                 125

<210> SEQ ID NO 16
<211> LENGTH: 341
<212> TYPE: PRT
<213> ORGANISM: Drosophila melanogaster

<400> SEQUENCE: 16

Ser Ser Ala Thr Leu Ser Pro Pro Ile Thr Pro Val Thr Pro Asp Pro
1               5                   10                  15

Ser Thr Ser Ala Gln Ser Thr His Phe Pro Phe Leu Ala Asp Ser Ala
            20                  25                  30

Ala Thr Ala Asn Ser Leu Leu Met Gln Arg Gln Tyr His Tyr His Leu
        35                  40                  45

Leu Leu Gln Gln Gln Gln Gln Leu Ala Met Ala Gln His Gln Leu Ala
    50                  55                  60

Leu Ala Ala Ser Ala Ala Ala Ser Ala Ser His Gln Gln Thr Asp
65                  70                  75                  80

Glu Ile Ala Arg Ser Leu Lys Ile Phe Ala Gln Val Thr Thr Gly Ala
                85                  90                  95

Ala Glu Asn Ala Ala Gly Ser Met Gln Asp Val Met Gln Glu Phe Ala
            100                 105                 110

Thr Asn Gly Tyr Ala Ser Asp Asp Leu Gly Arg Met Ser Tyr Gly Ser
        115                 120                 125

Ala Pro Pro Gln Val Gln Met Pro Gln Gln Gln His Gln Gln
    130                 135                 140

Gln Gly Leu His Leu Pro Leu Gly Arg Asn Pro Ala Gln Leu Gln Thr
145                 150                 155                 160

Asn Gly Gly Asn Leu Met Pro Ile Pro Leu Ala Thr His Trp Leu Asn
                165                 170                 175

Asn Tyr Arg Glu His Leu Asn Asn Val Trp Arg Asn Met Ser Tyr Ile
            180                 185                 190

Pro Ala Ala Pro Asn Thr Met Gly Leu Gln Ala Gln Thr Ala Ala Thr
        195                 200                 205

Val Ser Thr Asn Leu Gly Val Gly Met Gly Leu Gly Leu Pro Val Gln
    210                 215                 220

Gly Glu Gln Leu Arg Gly Ala Ser Asn Ser Ser Asn Asn Asn Asn
225                 230                 235                 240
```

```
Asn Asn Lys Val Tyr Lys Arg Tyr Asn Ser Lys Ala Lys Glu Ile Ser
                245                 250                 255

Arg His Cys Val Phe Cys Glu Asn Asn Glu Pro Glu Ala Val Ile
            260                 265                 270

Asn Ser His Ser Val Arg Asp Asn Phe Asn Arg Val Leu Cys Pro Lys
            275                 280                 285

Leu Arg Thr Tyr Val Cys Pro Ile Cys Gly Ala Ser Gly Asp Ser Ala
        290                 295                 300

His Thr Ile Lys Tyr Cys Pro Lys Lys Pro Ile Ile Thr Met Glu Asp
305                 310                 315                 320

Ala Ile Lys Ala Glu Ser Phe Arg Leu Ala Lys Ser Ser Tyr Tyr Lys
                325                 330                 335

Gln Gln Met Lys Val
            340

<210> SEQ ID NO 17
<211> LENGTH: 267
<212> TYPE: PRT
<213> ORGANISM: Mus musculus
<220> FEATURE:
<221> NAME/KEY: MISC_FEATURE
<223> OTHER INFORMATION: ECRep1a

<400> SEQUENCE: 17

Met Glu Ala Phe Pro Trp Ala Pro Arg Ser Pro Arg Ala Arg Ala
1               5                   10                  15

Pro Ala Pro Met Ala Leu Val Pro Ser Ala Arg Tyr Val Ser Ala Ser
                20                  25                  30

Gly Pro Val His Pro Gln Pro Phe Ser Ser Trp Asn Asp Tyr Leu Gly
            35                  40                  45

Leu Ala Thr Leu Ile Thr Arg Ala Ser Asp Arg Gly Ser Pro His Glu
        50                  55                  60

Gly Pro Gly Pro Thr Ala Ala Gly Pro Thr Met Gly Pro Pro Glu Asp
65                  70                  75                  80

Asp Glu Asp Asp Gly Glu Glu Pro Glu Ala Gly Gly Arg Tyr Leu
                85                  90                  95

Gly Gly Ala Leu Glu Leu Arg Ala Leu Glu Leu Cys Ala Gly Pro Ala
            100                 105                 110

Glu Pro Gly Leu Leu Glu Glu Arg Phe Ala Glu Leu Asn Pro Phe Ala
        115                 120                 125

Gly Arg Ala Ala Ala Val Leu Leu Gly Cys Ala Pro Thr Ala Ser Thr
    130                 135                 140

Thr Ala Ala Ala Ser Thr Ala Glu Val Thr Pro Arg Glu Glu Pro
145                 150                 155                 160

Ser Pro Ala Trp Ala Ala Glu Pro Arg Leu His Ala Ala Ser Gly Ala
                165                 170                 175

Thr Ala Ala Arg Leu Leu Lys Pro Glu Leu Gln Val Cys Val Phe Cys
            180                 185                 190

Arg Asn Asn Lys Glu Ala Val Ala Leu Tyr Thr Thr His Ile Leu Lys
        195                 200                 205

Gly Pro Asp Gly Arg Val Leu Cys Pro Val Leu Arg Arg Tyr Thr Cys
    210                 215                 220

Pro Leu Cys Gly Ala Ser Gly Asp Asn Ala His Thr Ile Lys Tyr Cys
225                 230                 235                 240

Pro Leu Ser Lys Val Pro Pro Thr Val Arg Pro Pro Arg Ser
                245                 250                 255
```

Asn Arg Asp Ser Leu Pro Ser Lys Lys Leu Arg
            260                 265

<210> SEQ ID NO 18
<211> LENGTH: 263
<212> TYPE: PRT
<213> ORGANISM: Rattus norvegicus
<220> FEATURE:
<221> NAME/KEY: MISC_FEATURE
<223> OTHER INFORMATION: ECRep1a

<400> SEQUENCE: 18

Met Glu Ala Phe Pro Trp Ala Pro Arg Ser Pro Arg Arg Ala Arg Ala
1               5                   10                  15

Pro Ala Pro Met Ala Leu Val Pro Ser Ala Arg Tyr Val Ser Ala Ser
            20                  25                  30

Gly Pro Val His Pro Gln Pro Phe Ser Tyr Trp Asn Asp Tyr Leu Gly
        35                  40                  45

Leu Ala Thr Leu Ile Thr Arg Ala Ser Asp Arg Gly Ser Pro His Glu
    50                  55                  60

Gly Pro Gly Pro Thr Pro Ala Gly Pro Thr Leu Gly Pro Pro Glu Asp
65                  70                  75                  80

Asp Glu Asp Asp Asp Gly Asp Glu Pro Glu Ala Gly Gly Arg Tyr Leu
                85                  90                  95

Gly Gly Ala Leu Glu Leu Arg Ala Leu Glu Leu Cys Ala Gly Pro Ala
            100                 105                 110

Glu Ala Gly Leu Leu Glu Glu Arg Phe Ala Glu Leu Asn Pro Phe Ala
        115                 120                 125

Gly Arg Ala Ala Ala Val Leu Leu Gly Cys Ala Pro Ser Ala Ser Ala
    130                 135                 140

Ala Ser Thr Ala Glu Val Thr Pro Arg Glu Glu Pro Ser Pro Ala Trp
145                 150                 155                 160

Ala Ala Glu Pro Arg Leu His Ala Thr Ser Gly Ala Thr Ala Ala Arg
                165                 170                 175

Leu Leu Lys Pro Glu Leu Gln Val Cys Val Phe Cys Arg Asn Asn Lys
            180                 185                 190

Glu Ala Val Ala Leu Tyr Thr Thr His Ile Leu Lys Gly Pro Asp Gly
        195                 200                 205

Arg Val Leu Cys Pro Val Leu Arg Arg Tyr Thr Cys Pro Leu Cys Gly
    210                 215                 220

Ala Ser Gly Asp Asn Ala His Thr Ile Lys Tyr Cys Pro Leu Ser Lys
225                 230                 235                 240

Val Pro Pro Pro Thr Val Arg Pro Pro Arg Ser Thr Arg Asp Asn
                245                 250                 255

Leu Pro Ser Lys Lys Leu Arg
            260

<210> SEQ ID NO 19
<211> LENGTH: 136
<212> TYPE: PRT
<213> ORGANISM: Mus musculus
<220> FEATURE:
<221> NAME/KEY: MISC_FEATURE
<223> OTHER INFORMATION: ECRep1b

<400> SEQUENCE: 19

Met Asp Leu Pro Pro Phe Asp Met Trp Arg Asp Tyr Phe Asn Leu Ser
1               5                   10                  15

```
Gln Val Val Met Asp Ile Ile Gln Ser Arg Lys Gln Arg Gln Glu Gly
            20                  25                  30

Glu Val Ala Glu Glu Pro Asn Ser Arg Pro Gln Glu Lys Ser Glu Gln
            35                  40                  45

Asp Leu Glu Gly Tyr Pro Gly Cys Leu Ala Thr Ile Cys Asn Phe Cys
        50                  55                  60

Lys His Asn Gly Glu Ser Arg His Val Tyr Thr Ser His Gln Leu Lys
65                  70                  75                  80

Thr Pro Glu Gly Val Val Cys Pro Ile Leu Arg His Tyr Val Cys
                85                  90                  95

Pro Leu Cys Gly Ala Thr Gly Asp Gln Ala His Thr Leu Lys Tyr Cys
            100                 105                 110

Pro Leu Asn Ser Ser Gln Gln Ser Leu Tyr Arg Arg Ser Gly Arg Asn
            115                 120                 125

Ser Ala Gly Arg Arg Val Lys Arg
            130                 135

<210> SEQ ID NO 20
<211> LENGTH: 136
<212> TYPE: PRT
<213> ORGANISM: Rattus norvegicus
<220> FEATURE:
<221> NAME/KEY: MISC_FEATURE
<223> OTHER INFORMATION: ECRep1b

<400> SEQUENCE: 20

Met Asp Leu Pro Pro Phe Asp Arg Trp Arg Asp Tyr Phe Asn Leu Ser
1               5                   10                  15

Gln Val Val Leu Gly Ile Ile Gln Ser Arg Lys Gln Arg Leu Glu Asp
            20                  25                  30

Glu Val Ser Glu Glu Leu Ala Ser Arg Pro Gln Gly Met Ser Glu Arg
            35                  40                  45

Gly Leu Glu Val Ser Pro Gly Ser Leu Ala Thr Ala Cys Asn Phe Cys
        50                  55                  60

Lys His Asn Gly Glu Ser Arg His Val Tyr Thr Ser His Gln Leu Lys
65                  70                  75                  80

Thr Pro Glu Gly Val Val Cys Pro Ile Leu Arg His Tyr Val Cys
                85                  90                  95

Pro Leu Cys Gly Ala Thr Gly Asp Gln Ala His Thr Leu Lys Tyr Cys
            100                 105                 110

Pro Leu Asn Ser Ser Gln Gln Ser Leu Tyr Arg Arg Ser Gly Arg Asn
            115                 120                 125

Ser Ala Gly Arg Arg Val Lys Arg
            130                 135

<210> SEQ ID NO 21
<211> LENGTH: 172
<212> TYPE: PRT
<213> ORGANISM: Mus musculus
<220> FEATURE:
<221> NAME/KEY: MISC_FEATURE
<223> OTHER INFORMATION: ECRep1c

<400> SEQUENCE: 21

Met Gly Thr Phe Asn Leu Trp Thr Asp Tyr Leu Gly Leu Ala Arg Leu
1               5                   10                  15

Val Gly Ala Leu His Lys Glu Glu Leu Asp Val Arg Leu Asp Pro
            20                  25                  30
```

```
Lys Pro Glu Pro Lys Pro Ser Ser Glu Ser Gln Gln Ala Ser Lys Glu
            35                  40                  45

Ser Ser Ala Ala Pro Glu Arg Leu Cys Ser Phe Cys Lys His Asn Gly
         50                  55                  60

Glu Ser Arg Ala Ile Tyr Gln Ser His Val Leu Lys Asp Glu Ala Gly
 65                  70                  75                  80

Arg Val Leu Cys Pro Ile Leu Arg Asp Tyr Val Cys Pro Gln Cys Gly
                 85                  90                  95

Ala Thr Gln Glu His Ala His Thr Arg Arg Phe Cys Pro Leu Thr Ser
            100                 105                 110

Gln Gly Tyr Thr Ser Val Tyr Cys Tyr Thr Thr Arg Asn Ser Ala Gly
            115                 120                 125

Lys Lys Leu Thr Arg Pro Asp Lys Ala Lys Thr Gln Asp Ala Gly His
            130                 135                 140

Arg Leu Gly Gly Glu Ala Ala Ala Gly Val Tyr Ala Gly Gly Leu Gly
145                 150                 155                 160

Val Gly Trp Arg Arg Leu Ser Val Phe Trp Gly Val
                165                 170

<210> SEQ ID NO 22
<211> LENGTH: 158
<212> TYPE: PRT
<213> ORGANISM: Rattus norvegicus
<220> FEATURE:
<221> NAME/KEY: MISC_FEATURE
<223> OTHER INFORMATION: ECRep1c

<400> SEQUENCE: 22

Met Gly Thr Phe Asn Leu Trp Thr Asp Tyr Leu Gly Leu Ala Arg Leu
 1               5                  10                  15

Val Gly Ala Leu His Glu Glu Glu Pro Asp Val Arg Leu Asp Pro
            20                  25                  30

Lys Pro Glu Pro Lys Pro Ser Ser Ala Ser Gln Gln Ala Ser Lys Glu
            35                  40                  45

Ser Ser Ala Ala Pro Glu Arg Leu Cys Ser Phe Cys Lys His Asn Gly
         50                  55                  60

Glu Ser Arg Ala Ile Tyr Gln Ser His Val Leu Lys Asp Glu Ala Gly
 65                  70                  75                  80

Arg Val Leu Cys Pro Ile Leu Arg Asp Tyr Val Cys Pro Gln Cys Gly
                 85                  90                  95

Ala Thr Gln Glu His Ala His Thr Arg Arg Phe Cys Pro Leu Thr Gly
            100                 105                 110

Gln Gly Tyr Thr Ser Val Tyr Cys Tyr Thr Thr Arg Asn Ser Ala Gly
            115                 120                 125

Lys Lys Leu Thr Arg Pro Asp Lys Ala Lys Thr Gln Asn Ala Gly His
            130                 135                 140

Arg Leu Gly Gly Glu Ala Ala Ala Gly Val Tyr Ala Gly Gly
145                 150                 155
```

What is claimed is:

1. An isolated amino acid sequence comprising SEQ ID NO:2.

* * * * *

UNITED STATES PATENT AND TRADEMARK OFFICE
CERTIFICATE OF CORRECTION

PATENT NO. : 7,569,668 B2  Page 1 of 1
APPLICATION NO. : 11/454605
DATED : August 4, 2009
INVENTOR(S) : Roy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 139 days.

Signed and Sealed this

Seventh Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,569,668 B2
APPLICATION NO. : 11/454605
DATED : August 4, 2009
INVENTOR(S) : Frans Van Roy et al.

Page 1 of 4

It is certified that error appears in the above-identified patent and that said Letters Patent is hereby corrected as shown below:

In the specification:

| | | |
|---|---|---|
| COLUMN 1, | LINE 9, | change "US20050089896A1 ,now" to --US20050089896A1, now-- |
| COLUMN 25, | LINE 54, | change "22" to --26-- |
| COLUMN 51, | LINE 58, | create new entries and insert after "155" |

```
--<210>  23
  <211>  51
  <212>  PRT
  <213>  Homo sapiens

<400>  23

Cys Val Phe Cys Arg Asn Asn Lys Glu Ala Met Ala Leu Tyr Thr Thr
  1               5                   10                  15

His Ile Leu Lys Gly Pro Asp Gly Arg Val Leu Cys Pro Val Leu Pro
              20                  25                  30

Arg Thr Thr Cys Pro Leu Cys Gly Ala Ser Gly Ile Asn Ala His Thr
              35                  40                  45

Leu Pro Thr
          50

<210>  24
  <211>  53
  <212>  PRT
  <213>  Xenopus laevis

<400>  24

Cys Gly Phe Cys Pro Ser Asn Arg Glu Ala Leu Ser Leu Tyr Thr Ser
  1               5                   10                  15
```

Signed and Sealed this
Ninth Day of April, 2013

Teresa Stanek Rea
*Acting Director of the United States Patent and Trademark Office*

CERTIFICATE OF CORRECTION (continued)
U.S. Pat. No. 7,569,668 B2

In the specification (continued):

```
        His Arg Leu Pro Ala Leu Asp Gly Pro Val Leu Cys Pro Val Leu Phe
                    20                  25                  30
        Gly Tyr Thr Cys Cys Pro Leu Cys Gly Ala Asn Gly Ile Trp Ala His
                    35                  40                  45
        Thr Met Arg Thr Thr
                    50

<210>   25
        <211>   52
        <212>   PRT
        <213>   Drosophila melanogaster

<400>   25

Cys Val Phe Cys Glu Asn Asn Asn Glu Pro Glu Ala Val Ile Asn Ser
        1               5                   10                  15
        His Ser Val Pro Asp Asn Phe Asn Arg Val Leu Cys Pro Lys Leu Pro
                    20                  25                  30
        Thr Thr Val Cys Pro Ile Cys Gly Ala Ser Gly Ile Ser Ala His Thr
                    35                  40                  45
        Leu Arg Thr Thr
                    50

<210>   26
        <211>   401
        <212>   PRT
```

CERTIFICATE OF CORRECTION (continued)

U.S. Pat. No. 7,569,668 B2

In the specification (continued):

<213> Drosophila melanogaster

<400> 26

| | | | | | | | | | | | | | | | |
|---|---|---|---|---|---|---|---|---|---|---|---|---|---|---|---|
| Met<br>1 | Phe | Arg | Ser | Asn<br>5 | Leu | Glu | Gly | Ser | Gly<br>10 | Ala | Ala | Ala | Val | Gly<br>15 | Val |
| Ala | Asn | Pro | Pro<br>20 | Ser | Leu | Ala | Gln | Ser<br>25 | Gly | Lys | Ile | Phe | Gln<br>30 | Leu | Gln |
| Asp | Asn | Phe<br>35 | Ser | Ala | Phe | His<br>40 | Ala | Arg | Gly | Gly | Leu<br>45 | Asn | Ile | Leu | Gly |
| Leu | Gln<br>50 | Asp | Met | Tyr | Leu<br>55 | Asp | Thr | Ser | Gly | Ala<br>60 | Asn | Ser | Ser | Ala | Thr |
| Leu<br>65 | Ser | Pro | Pro | Ile<br>70 | Thr | Pro | Val | Thr | Pro<br>75 | Asp | Pro | Ser | Thr | Ser | Ala<br>80 |
| Gln | Ser | Thr | His | Phe<br>85 | Pro | Phe | Leu | Ala | Asp<br>90 | Ser | Ala | Ala | Thr | Ala<br>95 | Asn |
| Ser | Leu | Leu | Met<br>100 | Gln | Arg | Gln | Tyr | His<br>105 | Tyr | His | Leu | Leu | Leu<br>110 | Gln | Gln |
| Gln | Gln | Gln<br>115 | Leu | Ala | Met | Ala | Gln<br>120 | His | Gln | Leu | Ala | Leu<br>125 | Ala | Ala | Ser |
| Ala | Ala<br>130 | Ala | Ala | Ser | Ala | Ser<br>135 | His | Gln | Gln | Thr | Asp<br>140 | Glu | Ile | Ala | Arg |
| Ser<br>145 | Leu | Lys | Ile | Phe | Ala<br>150 | Gln | Val | Thr | Thr | Gly<br>155 | Ala | Ala | Glu | Asn | Ala<br>160 |

CERTIFICATE OF CORRECTION (continued)
U.S. Pat. No. 7,569,668 B2

In the specification (continued):

```
Ala Gly Ser Met Gln Asp Val Met Gln Glu Phe Ala Thr Asn Gly Tyr
                165                 170                 175
Ala Ser Asp Asp Leu Gly Arg Met Ser Tyr Gly Ser Ala Pro Pro Gln
            180                 185                 190
Val Gln Met Pro Pro Gln Gln Gln His Gln Gln Gln Gln Gly Leu His
        195                 200                 205
Leu Pro Leu Gly Arg Asn Pro Ala Gln Leu Gln Thr Asn Gly Gly Asn
    210                 215                 220
Leu Met Pro Ile Pro Leu Ala Thr His Trp Leu Asn Asn Tyr Arg Glu
225                 230                 235                 240
His Leu Asn Asn Val Trp Arg Asn Met Ser Tyr Ile Pro Ala Ala Pro
                245                 250                 255
Asn Thr Met Gly Leu Gln Ala Gln Thr Ala Ala Thr Val Ser Thr Asn
            260                 265                 270
Leu Gly Val Gly Met Gly Leu Gly Leu Pro Val Gln Gly Glu Gln Leu
        275                 280                 285
Arg Gly Ala Ser Asn Ser Ser Asn Asn Asn Asn Asn Asn Asn Lys Val
    290                 295                 300
Tyr Lys Arg Tyr Asn Ser Lys Ala Lys Glu Ile Ser Arg His Cys Val
305                 310                 315                 320
Phe Cys Glu Asn Asn Asn Glu Pro Glu Ala Val Ile Asn Ser His Ser
                325                 330                 335
Val Arg Asp Asn Phe Asn Arg Val Leu Cys Pro Lys Leu Arg Thr Tyr
            340                 345                 350

Val Cys Pro Ile Cys Gly Ala Ser Gly Asp Ser Ala His Thr Ile Lys
            355                 360                 365
Tyr Cys Pro Lys Lys Pro Ile Ile Thr Met Glu Asp Ala Ile Lys Ala
    370                 375                 380
Glu Ser Phe Arg Leu Ala Lys Ser Ser Tyr Tyr Lys Gln Gln Met Lys
385                 390                 395                 400
Val--
```